ized

METHODS AND COMPOSITIONS FOR SUSTAINED DELIVERY OF DRUGS

CROSS-REFERENCE OF RELATED APPLICATION

This application claims priority to provisional application, U.S. Application No. 61/256,614, filed Oct. 30, 2009 and U.S. Application Ser. No. 61/289,471, filed Dec. 23, 2009, both of which are incorporated herein by reference thereto.

TECHNICAL FIELD

The present invention relates generally to methods and compositions for the controlled topical delivery of drugs. More specifically, the present invention relates to methods and compositions for delivery of one or more drugs to the eye, a specified area of the eye or systemically to a remote target by topical application to at least one upper eyelid and optionally at least one lower eyelid. More specifically, these methods comprise applying a preparation containing the desired drug or combination of drugs to the surface of at least one upper eyelid and optionally at least one lower eyelid, thereby causing transfer of the drug or drugs from the eyelid into the eye or systemic circulation via the vascular network within the eyelid.

BACKGROUND OF THE INVENTION

The treatment of human illness may be accomplished by administering drugs to the human body via various routes, e.g., oral, sublingual, rectal, parenteral, topical, inhalation, etc. The main advantage of topical delivery of drugs is convenience, with the added benefits that this delivery route avoids bypass metabolism, the risks and inconveniences of intravenous therapy and varied absorption rates and/or gastric emptying times. Topical delivery is generally defined as the application of a drug-containing formulation to the skin to directly treat cutaneous disorders, e.g., acne or the cutaneous manifestations of a general disease, e.g., psoriasis with the intent of containing the pharmacological or other effect of the drug to the surface of the skin or within the skin. Semi-solid formulations in all their diversity dominate the system for topical delivery, but foams, spray, medicated powders, solution, and even medicated adhesive systems are in use.

Topical delivery includes two basic types of product: (1) external topicals that are spread, sprayed, or otherwise dispersed on to cutaneous tissues to cover the affected area and (2) internal topicals that are applied to the mucous membrane orally, vaginally or on anorectal tissues for local activity. For the most part topical preparations are used for the localized effects at the site of their application by virtue of passive drug penetration into the underlying layers of skin or mucous membranes. Although some unintended drug absorption may occur, it is in sub-therapeutic quantities and generally of minor concern.

Under certain circumstances systemic delivery of drugs via topical application of drug-containing compositions to the skin is desirable. However, permeation across the skin first involves partitioning of the drug into the stratum corneum, a layer of the epidermis that is highly impermeable, particularly to hydrophilic molecules like peptides and proteins. For example, small peptides such as thyrotropin-releasing hormone (362 daltons) and vasopressin (356-358 daltons) are known to have difficulty in penetrating the skin barrier. Most substances are believed to diffuse across the stratum corneum via an intercellular lipoidal route, which is a tortuous pathway of limited frictional volume and even more limited productive fractional area in the plane of diffusion. Once through the stratum corneum, topically applied drugs must pass through the dermal region through a system of interlocking channels, through which diffusion is facile and without selectivity. Thus, transdermal systemic delivery of drugs is limited by the poor permeability of some drugs through the skin and limitations of size of drugs that can diffuse through the skin barrier, i.e., less than 500 Daltons. Moreover, because only limited amounts of drugs actually penetrate the skin layers even when penetration enhancers are applied, this route of administration can only be used for drugs that require very small plasma concentration to be effective. For example, the largest daily dose of drug in transdermal patch form is that of nicotine, at a dose of only twenty-one milligrams.

Topical administration of drugs to the eye for local delivery has been used successfully for years, e.g., eye drops for application directly to the eye or percutaneously absorptive compositions for passive diffusion across the skin or upper and/or lower eyelid, however, topical drug delivery for treatment of the posterior segments of the eye poses several problems. The posterior segments of the eye are exquisitely protected from the external environment, which poses unique and fairly challenging hurdles for drug delivery. In particular, the conjunctiva is a unique barrier within the eye with tight cell junctions which inhibit the passage of hydrophilic molecules. Even lipophilic molecules applied to the eye, for example in the form of eye drops, wash over the conjunctiva quickly, resulting in a true contact time of about ninety seconds or less, which is not enough time to permit large quantities to pass through the conjunctiva. It is somewhat dogmatic that topical ocular delivery is insufficient to achieve therapeutic drug levels in the posterior segments.

Topical delivery of drugs to the upper eyelid for local delivery to the anterior segments of the eye has been accomplished through inclusion of an amount of a vasoconstrictor in the topically applied composition or through application of the drug near or along the lash line, effectively applying the drug to the surface of the eyeball over time through blinking action. Inclusion of a vasoconstrictor in certain ophthalmic compositions, particularly those intended to treat glaucoma, for example, has significant drawbacks since the vasoconstrictor restricts blood flow in the immediate area of the eye as well as within the eye, thereby exacerbating the underlying condition.

Thus, there exists a need for methods and compositions for topical administration of drugs for local delivery, such as to the eye and particularly the posterior segments of the eye, as well as for systemic delivery.

SUMMARY OF THE INVENTION

In one aspect of the invention there is provided a method for topical administration of a drug or combination of drugs for systemic delivery thereof to a human patient comprising applying to at least one eyelid of a patient a composition comprising the drug or combination. In certain embodiments of this aspect of the invention the composition further comprises an effective amount of a muscle fasciculation agent, and optionally further comprises an effective amount of a permeability enhancer. In certain embodiments of this aspect of the invention, the muscle fasciculation agent is caffeine, theophylline, pentoxifyline or theobromide, which may be included in the topical composition in an amount of up to about 1% and in certain embodiments may be included in an amount of up to about 30 wt % or in certain other embodiments, up to about 50 wt % of the composition. In some embodiments the composition may further comprise in addition to a muscle fasciculating agent, from about 0.001 to 50 wt % of an ionotropic agent, such as digitalis.

In another aspect of the invention there is provided a method for topical delivery of a drug or combination of drugs to the eyeball, eyelid, anterior segments of the eye or posterior segments of the eye comprising applying to at least one eyelid of a human patient a composition comprising the drug or combination of drugs. In certain embodiments of this aspect of the invention the composition comprises an effective amount of a muscle fasciculation agent, and may further comprise an effective amount of a permeability enhancer, vasoconstrictor or a vasodilator or both. In certain embodiments, the drug or combination of drugs is a drug used for ophthalmic treatment, a systemic drug, a nutrient, hormone or other biological agent and in other embodiments each drug in the composition is 6000 Daltons or less. In other embodiments of this aspect of the invention, the muscle fasciculation agent is caffeine, theophylline, pentoxifyline or theobromide, which may be included in the topical composition in an amount of up to about 1% or in certain embodiments up to about 50 wt %. In addition to a muscle fasciculating agent, the compositions may include from 0.001 to 50 wt % of an ionotropic agent, such as digitalis.

In certain embodiments of this aspect of the invention, two different drugs are administered by application of a first drug to one eyelid and application of a second drug to the other eyelid. In other embodiments of the invention, uptake of the composition through the eyelid is manipulated by the applications of the compositions to different areas of the eyelid, e.g., application of a composition containing the active drug or combination of drugs to the middle portion of the eyelid, followed or preceded by application of a composition comprising a vasoconstrictor agent to the border of the eyelid.

In another aspect of the invention there is provided a method of treating glaucoma comprising topically applying a composition comprising a therapeutically effective amount of a β-antagonist, α-antagonist, prostaglandin analog, alpha-adrenergic agonist, carbonic anhydrase inhibitor, anti-cholinergic agent, vasodilator, or neuroprotective agent a combination thereof to one or both upper and optionally, lower, eyelids of a patient. In certain embodiments, the composition further comprises an amount of a muscle fasciculation agent, such as caffeine, theophylline, pentoxifyline or theobromide effective to facilitate delivery of the drug to the posterior segment of the eye, and optionally an effective amount of a permeability enhancer. In some embodiments the composition may further comprise in addition to a muscle fasciculating agent, from about 0.001 to 50 wt % of an ionotropic agent, such as digitalis.

In another aspect of the invention there is provided a method of treating dry eye comprising topically applying a composition comprising a therapeutically effective amount of a parasympathomimetic cholinergic agent (e.g., Pilocarpine, Cevimeline, Carbachol), anticholinesterase (e.g., Echothiophate Iodidide, Isofluorophate, Demecarium Bromide, Physostigmine, Neostigmine, Pyridostigmine, Edrophonium), androgen, estrogen, B-agonist (e.g., isoproternol), alpha-agonist (e.g., phenylepherine, ephedrine, and the like (alone or in combination) and from 0.001% to 50 wt % of a muscle fasciculating agent to one or both upper and optionally lower eyelids of a human patient. In certain embodiments, the muscle fasciculation agent is caffeine, theophylline, pentoxifyline or theobromide effective and in another embodiment, the composition further comprises an effective amount of a permeability enhancer. In some embodiments the composition may further comprise in addition to a muscle fasciculating agent, from about 0.001 to 50 wt % of an ionotropic agent, such as digitalis.

In other aspects of the invention, the present method and composition comprising the appropriate drug(s) or therapeutic agent(s) in therapeutically effective amount(s) and a therapeutically effective amount of a micro fasciculating agent is applied for the treatment of an eye disease or condition such as blepharitis, floppy eyelid syndrome, trachomatous dry eye, retinopathy, retinal degeneration, nasolacrimal duct obstruction, epiphora, chalazion, hordeolum, allergic conjunctivitis and keratitis, keratopathy, corneal degeneration, cataract, infectious conjunctivitis and keratitis, pterygium, pinguiculum, iritis, uveitis, keratitis, vitritis, vitreous floaters, vitreous detachment, vitreous hemorrhage, retinal detachment, sub retinal hemorrhage, choridal neovascular membrane, retinal edema, macular edema, diabetic retinopathy, retinal hemorrhage, choridal malignancy, orbital malignancy, eyelid tumors, optic neuritis, optic neuropathy, strabismus, refractive error, glaucoma and the like, lacrimal gland disorders, aging-related ophthalmic conditions.

In yet another aspect of the invention, the present method and compositions comprising an appropriate drug or therapeutic agent or combinations of drugs or therapeutic agents is applied to one or more eyelids to achieve a therapeutically sustainable systemic concentration of therapeutic agent/drug/combination to treat a condition or disease remotely removed from the site of application, e.g., diabetes, systemic infection, kidney disease, hypertension, heart disease, nicotine withdrawal, or for administration of hormone replacement therapy.

In another aspect of the invention, a method of treating an ophthalmic condition is provided in which a composition comprising therapeutically effective amount of one or more active agents for the treatment of the ophthalmic condition and a therapeutically effective amount of a vasodilator and optionally a therapeutically effective amount of a muscle (or micro) fasciculatinging agent is topically applied to one or more eyelids of a patient in need thereof. In certain embodiments of this aspect of the invention the vasodilator is a phosphodiesterase inhibitor. In some embodiments the composition may further comprise in addition to a muscle fasciculating agent, from about 0.001 to 50 wt % of an ionotropic agent, such as digitalis.

In another aspect of the invention there is provided a method and composition for treating cataracts and/or maintaining the health of the idea. The methods and compositions of this aspect of the invention comprise topically applying to the outer surface of at least one eyelid of a human patient an ophthalmic composition comprising from about 0.001 to 50 wt % caffeine as the sole active agent. In certain embodiments, the composition is applied to at least one eye one time per day. In certain embodiments, the composition comprises from 10 to 500 mg caffeine. In other embodiments of this aspect of the invention, the composition further comprises from about 0.001 to 50 wt % of an ionotropic agent.

In another aspect of the invention there is provided a kit for percutaneous eyelid administration of one or more therapeutic agents comprising an applicator and a topical composition or compositions comprising one or more therapeutic agents. In certain embodiments of this aspect of the invention the applicator is a patch containing a composition of the invention on the surface to be applied to the eyelid; a rollerball applicator integrally connected to a container in which the composition is contained; an applicator strip comprising a composition of the invention on the surface to be applied to the eyelid; a pliable finger cot containing a composition of the invention as a blister positioned on the tip thereof; or an applicator for dipping into a solution of a composition of the invention or an eye stick (structurally similar to lipstick, but for application to the outer surface of the upper/lower eyelid).

In another aspect of the invention there is provided a method and compositions for topical transdermal drug delivery comprising administering to the outer surface of the epidermis of an individual a composition comprising the drug and a muscle fasciculating agent. In certain embodiments the composition further comprises a permeability enhancer. In certain embodiments of this aspect of the invention, the muscle fasciculating agent is caffeine, theophylline, pentoxifyline or theobromide, which may be included in the topical composition in an amount of up to about 1% and in certain embodiments may be included in an amount of up to about 30 wt % or in certain embodiments, up to about 50 wt % of the composition. In some embodiments the composition may further comprise in addition to a muscle fasciculating agent, from about 0.001 to 50 wt % of an ionotropic agent, such as digitalis. In certain embodiments of this aspect of the invention the drug is fewer than 6000 Daltons in size and in other embodiments the drug is greater than 6000 Daltons in size.

In another aspect of the invention there are provided compositions and methods for enhancing the uptake and providing sustained release of a therapeutic agent comprising topically administering to at least one eye of a patient a composition comprising the therapeutic agent and a muscle fasciculating agent, wherein the composition contacts the underside of the eyelid of the at least one eye. In certain embodiments the composition further comprises a permeability enhancer. In certain embodiments of this aspect of the invention, the muscle fasciculating agent is caffeine, theophylline, pentoxifyline or theobromide, which may be included in the topical composition in an amount of up to about 1% and in certain embodiments may be included in an amount of up to about 30 wt % or in certain embodiments, up to about 50 wt % of the composition. In some embodiments the composition may further comprise in addition to a muscle fasciculating agent, from about 0.001 to 50 wt % of an ionotropic agent, such as digitalis.

DETAILED DESCRIPTION OF THE INVENTION

Figure 1:
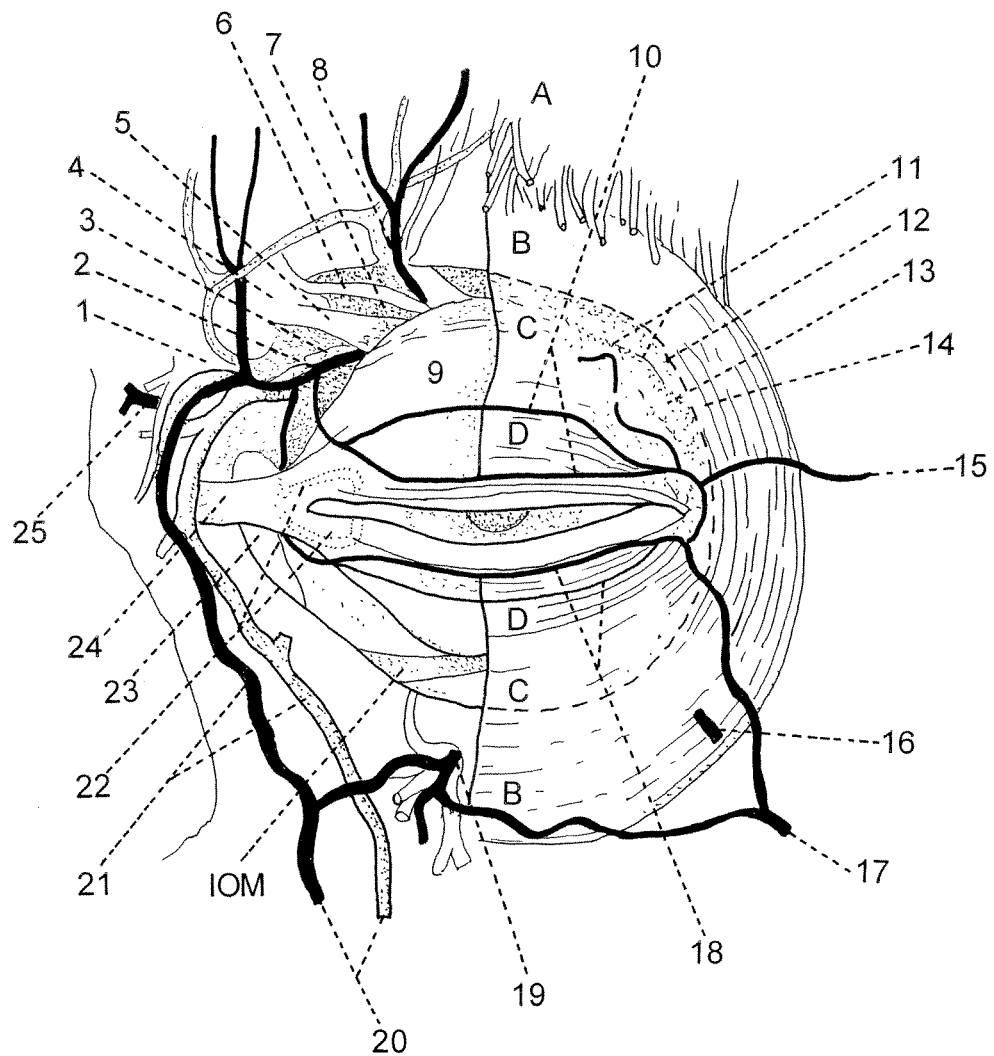
FIG. 1 is a front view of the left eye, showing (1) the infratrochlear nerve; (2) ophthalmic (orbital) artery; (3) nasocilliary nerve; (4) trochlea; (5) tendon of superior oblique muscle; (6) supratrochlear nerve; (7) superior orbital vein; (8) supraorbital artery, vein and nerve; (9) levator aponeurosis; (10) peripheral and marginal arterial arcades of upper lid; (11) lacrimal artier and nerve terminal branches; (12) orbital lobe of lacrimal gland; (13) palpebral lobe of lacrimal gland; (14) zygomaticotemporal nerve; (15) anterior branch of temporal artery; (16) zygomaticofacial artery and nerve; (17) malar branch of transverse facial artery; (18) peripheral and marginal arterial arcades of lower lid; (19) infraorbital artery and nerve; (20) facial artery and vein; (21) angular artery and vein; (22) canaliculi; (23) lacrimal sac; (24) medial canthal tendon-anterior attachment; and (25) dorsal nasal artery.

The present inventive methods, kits and compositions utilize transport via vascular collaterals or channels within the eyelid to deliver therapeutic agents to specific target tissues that receive blood supply, such as glands, conjunctiva, periocular tissue, the eye including the posterior segments thereof, and even remote target sites via the systemic circulation. The inventors have discovered that topical application of the therapeutic compositions of the invention to the outer surface of the upper eyelid or eyelids and optionally to at least one lower eyelid of a human patient greatly aids absorption of any therapeutic agent. The eyelid is unique in having scant stratum corneum, the epidermis surface layer that retards drug absorption, a very thin epidermis (approximately 40 microns), and no subcutaneous fat. Muscle fibers of the Orbicularis muscle that cause the eyelid to blink shut are directly beneath the dermis and these muscle fibers can assist drug delivery by in-pumping drugs through the muscle and it's vascular system. The inventors have discovered that these four factors coupled with a rich circulatory network within the eyelid that can be accessed by the applied drug via the vascular dermis allow percutaneous absorption of a wider variety of drugs to therapeutic levels compared to application of drugs via other routes. Thus, drugs and other therapeutic agents can be applied to the outer skin surface of the eyelid (or the skin of the underside of the eyelid by way of applying an eye drop directly to the eye) to specifically target the eyelid glands (accessory lacrimal, lacrimal, meibomian, glands of zeiss and moll); conjunctival goblet cells, which secrete the mucinous layer of the tear film; the sub-conjunctival space and conjunctival epithelium; or periocular tissues for drug delivery to these tissues or to the entire eyeball itself. Moreover, the present methods, kits and compositions can be utilized to achieve systemic uptake of therapeutic agent while bypassing the gastrointestinal (GI) tract and first pass hepatic metabolism.

As used herein the term "drug" means any chemical substance used in the treatment, cure, prevention, or diagnosis of disease or used to otherwise enhance physical or mental well-being. The term "therapeutic agent" is also used to denote any compound, molecule, or substance used for the medical treatment of a disease or condition.

The term "eyelid" as used herein means particularly the upper eyelid(s) of a human subject, but may include the lower eyelid(s) as well. It is understood that in each embodiment of the present methods the appropriate therapeutic agent is applied to the outer skin surface of at least one upper eyelid and optionally to at least one lower eyelid unless expressly stated otherwise.

The term "muscle fasciculating agent" or "micro fasciculating agent" as used herein means any agent that causes a small, local involuntary muscle contraction (a muscle twitch) such as caffeine, theophylline, pentoxifyline or theobromide.

The term "sustained release" is used herein in its ordinary sense to mean that the compositions of the invention are designed to release a drug slowly over an extended period of time.

In certain aspects, the present methods and compositions take advantage of the unique human upper eyelid anatomy to target drug delivery. The major anatomic landmark and demarcation of the upper eyelid is the anteroposterior fascial fusion of the orbital septum and levator aponeurosis (collagen and elastic fiber extension of the levator muscle that elevates the eyelid) in the superior aspect of the eyelid. This tissue fuses inferiorly with the connective tissue "backbone" of the upper eyelid called the tarsus. Therefore, the upper eyelid is classified as having two compartments: one that is "preseptal and post-septal" in the superior aspect of the upper eyelid and "pretarsal and post-tarsal" in the inferior aspect of the upper eyelid. These separate anatomic and physiologic compartments are not only basic anatomical dogma, but form the critical landmarks used in surgery. Our understanding of physiological functions of the essential function of the upper eyelid in maintaining secretory tear function and mechanical protection are based upon these well understood anatomical barriers.

Transdermal eyelid drug delivery systems to date have relied almost exclusively on the principle of passive diffusion to transport highly lipid-soluble hormones such as the androgens and estrogens/progestins or small molecules, i.e., less than 500 Daltons to permeate in an untargeted manner throughout the eyelid tissue or have included amounts of vasoconstrictors to facilitate drug absorption in an untargeted manner. Due to the rigid anatomical barriers that exist within the upper eyelid and to a lesser degree in the lower eyelid, prior methods of topical drug delivery via the outer surface of the upper (or lower) eyelid have not been satisfactory in regards to targeted drug delivery to certain segments of the eye (thus have not successfully targeted the entire eyeball) and have not achieved successful systemic delivery of therapeutic amounts of drug or other therapeutic agents.

In contrast, the methods, kits and compositions of the present invention disregard the preconceived dogma regarding anatomical barriers and compartments of the eyelids, particularly of the upper eyelid. Although these compartments and barriers clearly exist, they are connected by the vascular supply between the two main circulatory systems of the eyelid. These two systems in a broadest sense derive from the internal carotid artery and the external carotid artery system. The vascular branches from these two main arteries provide the eyelid a rich dual blood supply. The internal carotid branches supply the inner posterior "post-septal and post-tarsal" compartment and the external carotid branches serve the outer anterior "preseptal and pretarsal" compartment.

The present inventors discovered that these two circulatory systems, which are extensively linked in the upper eyelid via rich vascular anastomoses can be utilized in the present methods, compositions and kits as a vehicle for transdermal drug delivery from the upper eyelid to specifically target the accessory lacrimal glands, conjunctival mucosal secretory apparatus, meibomian glands, the sub-conjunctival space of the palpebral conjunctiva that reflects into the sub-bulbar conjunctival space and to access the periocular and transscleral pathways for targeting with certain therapeutic drugs. Furthermore, gravity, which moves drugs applied to the eyelid inferiorly, is an advantage to the present invention in regards to drug delivery to periocular tissue and conjunctiva. Application of the compositions of the present invention to the upper eyelid results in greater bioavailability of the therapeutic agent(s) with a large surface area in this setting of gravitational advantage. Once the therapeutic agent(s) is secreted into the peri-conjunctival space, the upper eyelid provides a unique mechanical spreading action to the agent(s). Finally, the present drug delivery method reaches any area of the body that is supported by the vasculatory network.

The present invention overcomes several insufficiencies of prior methods for subcutaneous or topical delivery of therapeutic agents. For example, the most commonly used non-invasive method for treating the vast majority of eye diseases and conditions is through the use of eye drops, which are difficult for most people to apply accurately and are washed out or diluted by the tear reflex, reducing the drug's ability to remain in contact with and penetrate the eye. In fact, eye drops are eliminated from the precorneal area in 90 seconds or less, which is so short an exposure period, especially for hydrophilic drugs, that the naturally occurring spaces between epithelial cells (e.g., the paracellular route of drug delivery) are too widespread and coincidental to rely on for drug delivery therethrough. Thus, eye drops generally result in delivery of only about 1-5% of the topically administered therapeutic agent. Consequently, most eye drops contain an amount of preservative which functions to punch holes in the corneal epithelium to improve absorption. Such agents are inherently toxic to the richly enervated epithelium and cause pain and discomfort to patients. Moreover, eye drops must be manufactured within a very narrow pH range, which limits the types of drugs that can be delivered via this non-invasive route.

Topical delivery of ophthalmic drugs to the eyelid of a patient has been used previously with limited success. Application of olapatadine, epinastine and muscarinic receptor agonists, small molecules of less than 500 Daltons to the surface of the eyelid has been reported to achieve sustained delivery of the drug to the anterior segment of the treated rabbit eye (US 2009/0209632, US 20090143359 and US 2007/0053964, respectively). It is disclosed in each of these patent applications that the amount of release of olapatadine, epinastine or muscarinic receptor agonist to the anterior segment of the eye is controlled by manipulation of the amount of the drug and/or skin permeability through the use of known permeability enhancers for application directly to the anterior segment of the eye, rather than through systemic blood flow. Systemic absorption was not observed by these prior methods and hence, delivery to systemic tissues, the contralateral untreated eye, and the entire treated eyeball including the posterior segments of the eye was not achieved.

WO 2008/026756 discloses an ophthalmic percutaneous absorption composition for administration to the eyelids which contains a vasoconstrictor as an essential component necessary to achieve delivery of therapeutic agent to the anterior segments of the eye. It is specifically disclosed that the vasoconstrictor need only have blood vessel contracting activity in order to effect delivery of the drug into the anterior segment of the eye. The necessity for inclusion of a vasoconstrictor is disadvantageous for treatment of the eye since these agents decrease blood flow, which in turn causes visual damage from diseases where ischemia (poor oxygenation and blood flow) plays a role such as glaucoma, diabetic retinopathy, retinal degeneration, or vascular disease for example.

In contrast, the present inventors have discovered that sustained release and delivery of therapeutic agent to the systemic blood flow and/or all regions of the eye, including the heretofore inaccessible posterior sections of the eye, can be achieved by topical application of the therapeutic agent(s) to the outer surface of one or both upper eyelids and optionally, one or both lower eyelids. The inventors have discovered that application of a therapeutic compound or drug to one eye (the treated eye) results in drug delivery to the untreated contralateral eye as well, via the systemic circulatory system. Moreover, any drug or therapeutic agent having a molecular weight up to and exceeding 6000 Daltons can be administered in this manner and achieve therapeutic concentration at the target site, even when the target site is remote from the eyelid, i.e., via the systemic circulatory system or located within the posterior segments of the eye.

The compositions of the invention comprise a therapeutically effective amount of drug appropriate for the condition or disease to be treated. In general, the compositions of the invention comprise therapeutic agent in amounts of from about 0.01 to about 40 wt % of the composition in a pharmaceutically acceptable carrier suitable for application to the outer skin surface of the eyelid. The dose and treatment regimen, including administration period of the compositions of the invention vary depending on the target disease, symptom, patient, administration route and the like. The therapeutic agents useful for the present invention may be synthetic drugs or may be naturally derived or derivatized. For example, tinctures and natural extracts containing therapeutic agents may be employed in the compositions and methods of the invention. For example, for the treatment of glaucoma, a cream, gel, spray, lotion, ointment, stick applicator, foam, film, or an adhesive formulation for example containing latanoprost in an amount of about 0.1 to 40 wt % of the composition is applied to the upper eyelid. The inventors have discovered that application of latanoprost to the upper eyelid (and optionally lower eyelid) results in a significant and semi-permanent decline in intraocular pressure in both the treated and untreated eye (although a somewhat greater decline in the treated eye was observed), indicating that the number of applications of latanoprost to achieve the target intraocular pressure can be decreased, e.g., from once per day to once every two to four days or longer. The treatment period will vary depending upon the condition being treated and the therapeutic agent or drug being applied, but in general will range from about one day to three months.

In certain embodiments of the invention a muscle contractility agent (a muscle or micro fasciculating agent) is included in the therapeutic compositions, such as caffeine, theophylline, pentoxifyline, theobromide. The micro fasciculating agent may be included in an amount up to about 50 wt % and this amount will vary depending on the target site for drug delivery, e.g. higher amounts of the micro fasciculating agent may be included when the target is remote (and delivery is achieved systemically) or if the target site is the posterior segment of the eye or for sustained delivery. For example, for systemic delivery of drug via application to one or both upper eyelids an amount of about 1% by weight or more of a micro fasciculating agent may be included in the composition, while for those embodiments where delivery of therapeutic agent to the posterior segment of the eye is desired, an amount of about 0.5 to 50 wt %, such as for example 5 wt % of a micro fasciculating agent may be included in the composition. In certain embodiments, particularly those in which the delivery of therapeutic agent to the anterior portion of the eye is desired, the amount of micro fasciculating agent in the composition is in the range of from 0 to 5%, and in other embodiments from 0.001 to 5%. In certain embodiments, particularly when sustained release of the therapeutic agent is desired, the composition may contain up to about 50 wt % of a muscle fasciculating agent. In certain embodiments the muscle fasciculating agent is an appropriate amount of caffeine, which has the benefit of being a naturally occurring and readily metabolized small molecule.

In certain embodiments of the invention, an ionotropic agent may be included in the compositions in addition to a muscle fasciculating agent. Ionotropic agents include any of a class of agents affecting the force of muscle contraction. Positive inotropic agents increase, and negative inotropic agents decrease the force of skeletal muscle contraction. The ionotropic agent may be added in an amount of from about 0.001 to 50% and the selection of the particular ionotropic agent is made on the basis if the desired effect on muscle contraction. Non-limiting examples of positive inotropic agents that may be included in the compositions of the invention include Berberine, Bipyridine derivatives, Inaminone, Milrinone, Calcium, Calcium sensitisers, Levosimendan, Cardiac glycosides, Digoxin, Catecholamines, Dopamine, Dobutamine, Dopexamine, Epinephrine (adrenaline), Isoprenaline (isoproterenol), Norepinephrine (noradrenaline), Eicosanoids, Prostaglandins, Phosphodiesterase inhibitors, Enoximone, Milrinone, Theophylline, and Glucagon. In certain embodiments of the invention, digitalis is included in the compositions as an ionotropic agent.

The ophthalmic therapeutic compositions of the invention that do not include a micro fasciculation agent may contain one or more of a vast array of ophthalmic therapeutic agents, alone or in combination, but such therapeutic agents do not include olapatadine, muscarinic receptor agonists or epinastine, unless such compositions also include a vasodilator and/or vasoconstrictor.

In those aspects of the invention described above, the methods and compositions take advantage of the extensively linked circulatory systems in the upper eyelids through application of the therapeutic composition to the outer surface of the eyelid(s). However, the inventors have discovered that inclusion of a muscle fasciculating agent in any ophthalmic composition for direct topical delivery to the eye that upon application to the eye comes into contact with the underside of the eyelid skin enhances uptake and sustained release of the drug(s) included in the ophthalmic composition. Thus, typical eye drop formulations and gels, for example, that are formulated for direct application to the eye, are improved by addition of an amount of from about 0.01 to up to 50 wt % of a muscle fasciculating agent and optionally, an ionotropic agent. Such eye drop formulations are encompassed by the present invention.

Vasoconstrictor as an active drug: In certain embodiments of the invention the sole therapeutic agent(s) of the topical composition is one or more vasoconstrictors. Compositions containing vasoconstrictor as the sole therapeutic agent(s) are applied to at least one upper eyelid and optionally at least one lower eyelid of the patient for the treatment of conditions including, but not limited to, redeye, allergic conjunctivitis, blepharitis, puffy eye lids and any disease state or condition that includes as a symptom edema, vasodilation and/or bleeding in the eyelid, anterior segment, posterior segment or orbit of the eye. In some embodiments, such vasoconstrictor-containing compositions may also contain from 0 to 1% or more as required of a micro fasciculating agent, such as for example, caffeine, theophylline, pentoxifyline or theobromide and/or a permeation enhancer agent. Further, vasoconstrictors may be combined with other active agents, and/or micro fasciculating agent, permeation agent, and the like. Although any vasoconstrictor may be used in the compositions and methods of the present invention, certain embodiments employ a therapeutically effective amount of ephedrine. Other embodiments of this aspect of the invention include use of a vasoconstrictor such as for example methoxamine, phenylyephrine, oxymetazoline, cocaine, Allerest®, naphazoline, Visine®, tetrahydrolozine, Op-Thal-Zin/zinc sulfate, Rhindecon, phenylpropanolamine, Sudafed®, pseudoephedrine, Ephed II, ephedrine, Aramine, metaraminol, Epifrin, epinephrine, Levophed, norepinephrinand nicotine.

In those embodiments of the invention in which a vasoconstrictor is included in the topical treatment regimen, the vasoconstrictor may be applied to the eyelid separate from a second topical composition comprising other active agents, microfascilitating agent, optional permeating agent and optional ionotropic agent. The vasoconstrictor containing composition may be applied to the same area of the eyelid as the second topical composition or may instead be applied to the perimeter of the area of the eyelid onto which the second topical composition was applied. Application to the perimeter region is believed to limit the effects of the vasoconstrictor and thereby limit any unwanted side effects, while limiting systemic flow of the active agent. Application of a vasoconstrictor and active agent in this manner may be achieved through use of separate applicators or through application of a composition formulated as a stick applicator (an "eyelid-stick") in which the active ingredients (other than vasoconstrictor), any permeating agents, muscle fasciculating agent and/or ionotropic agnet comprise the middle of the eyelid-stick and the perimeter of the eyelidstick comprises the vasoconstrictor, resulting in application of a small amount of vasoconstrictor on the perimeter of the application area. In another embodiment, the vasoconstrictor is impregnated on the border of an eyestrip or film applicator with active agent(s), and/or micro fasciculating agent, ionotropic agent and/or permeating agent impregnated in the middle of or throughout the entire applicator. Application of the strip to the eyelid and subsequent removal results in localized application of the various components (e.g., a border of vasoconstrictor).

Vasodilator as the active drug: Classes of vasodilator agents that may be included in the compositions as the sole therapeutic agent(s) or in combination with a vasoconstrictor or other therapeutically active agent include alpha-blockers (alpha-adrenoreceptor antagonists), ACE inhibitors (angiotensin converting enzymes), angiotensin receptor blockers, β2 agonists (β2-adrenoceptor agonists), calcium channel blockers, centrally acting sympatholytics, direct acting vasodilators, endothelin receptor antagonists, ganglionic blockers, nitrodilators, phosphohodiesterase inhibitors, potassium channel openers, and rennin inhibitors. Specific examples of vasodilators that may be used in the methods and compositions of the invention include, but are not limited to: arginine, bencyclane fumarate, benzyl nicotinate, buphenine hydrochloride, ciclonicate, cyclandelate, ethyl nicotinate, hepronicate, hexyl nicotinate, hydralazine, inositol nicotinate, isoxsuprine hydrochloride, methyl nicotinate, minoxidol, naftidrofuryl oxalate, nicametate citrate, niceritrol, nicoboxil, nicofuranose, nicotinyl alcohol, nicotinyl alcohol tartrate, nitric oxide, nitroglycerin, nonivamide, oxpentifylline, papaverine, papaveroline, pentifylline, peroxynitrite, pinacidil, sodium nitroprusside, suloctidil, teasuprine, thymoxamine hydrochloride, tolazoline, vitamin E nicotinate, and xanthinol nicotinate. Centrally acting vasomodulatory agents include clonidine, quanaberz, and methyl dopa. Alpha-adrenoceptor blocking agents include indoramin, phenoxybenzamine, phentolamine, and prazosin. Adrenergic neuron blocking agents include bedmidine, debrisoquine, and guanethidine. ACE inhibitors include benazepril, captopril, cilazapril, enalapril, fosinopril, lisinopril, perindopril, quinapril, and ramipril. Ganglion-blocking agents include pentolinium and trimetaphan. Calcium channel blockers include amlodipine, diltiazem, felodipine, isradipine, nicardipine, nifedipine, nimodipine, and verapamil. Prostaglandins including: prostacyclin, thrombuxane A2, leukotrienes, PGA, PGA1, PGA2, PGE1, PGE2, PGD, PGG, and PGH. Angiotensin II analogs include saralasin. Such compounds may be applied to the eyelid as the sole active component of a topical composition with or without any of a micro fasciculating agent, permeating agent or ionotropic agent for therapeutic treatment of the posterior segment of the eye, to treat the optic nerve or retina, for example or to treat conditions such as glaucoma, ischemic retinopathy (diabetic, hypertensive, degenerative) and the like.

Compositions containing a therapeutically affective amount of a vasodilator, as the sole active agent or in combination with other therapeutically active agents, and optional micro fasciculating agent, ionotropic agent and/or permeating agent may be used in the treatment of a variety of ophthalmic conditions by application to at least one eyelid of a patient in need thereof. The vasodilator species and concentration within the transdermal drug delivery formulation may be different for each drug and for each delivery requirement. There may be one or more vasodilator, acting in a similar or different mechanism within the same formulation. There may also be vasodilators that are added in tandem temporally or simultaneously to induce the optimal reaction and to create a tissue concentration profile of the vasodilators that optimizes the transdermal transportation of the drug into the tissue or the bloodstream. The vasodilator may serve exclusively as the vasodilation agent or it may also, in addition, serve other functions to the delivery complex such as to assist in the penetration of the active drug molecule or the penetration of the other components of the delivery vehicle. The vasodilator may also co-function by definition and by action as the active drug agent, or to a serve another undefined function to create the optimal chemistry of the delivery vehicle formulation.

In another embodiment of this aspect of the invention, a vasodilator and vasoconstrictor may be used in combination in the compositions and methods of the invention. For example, an active drug, vasodilator, and vasoconstrictor in a formulation, optionally with a penetrating, ionotropic agent and/or micro fasciculating agents can be applied to the eyelid. The time release aspect of the vasodilator and vasoconstrictor affects both drug delivery destination and activation. In another embodiment, a fast acting vasodilator is employed in the compositions and methods to immediately increase blood flow and, therefore, increase drug absorption immediately upon drug application. This may be followed by topical application to the same eyelid(s) of a delayed acting vasoconstrictor which acts to sequester the drug at the treated site/eyeball thereby preventing systemic absorption and increasing local activity of drug. In yet another embodiment, a short acting vasoconstrictor is applied to at least one upper eyelid to prevent systemic blood flow followed by application to the eyelid of a delayed acting vasodilator, which then causes increased delivery systemically. Additionally, since vasoconstrictor use decreases blood flow locally to the eye and often results in worsening of ischemic eye diseases such as glaucoma or diabetic retinopathy, the use of a vasodilator in combination therewith serves to diminish this negative effect while enabling the use of the least amount of vasoconstrictor necessary.

Caffeine as the active drug. Caffeine has been shown to have certain anti-oxidant properties and to provide protection against cataract formation and reduce cataracts in test animals when applied directly to the eye in the form of eye drops. Application of caffeine to the outer surface of at least one eyelid of a human patient via the methods and compositions of the invention eliminates the unpleasant effects of eye drops and results in delivery of higher concentrations of caffeine to the target site within the eye than is attainable with eye drops, which are primarily washed away by blinking. Moreover, because caffeine causes micro fasciculation in the eyelid muscle, sustained release of caffeine is attained by application of the composition directly to one or both eyelids. Consequently, the caffeine composition need only be applied once per day in many instances, although multiple applications per day are also contemplated depending on the physical condition of the treated eye(s).

The caffeine containing compositions of this aspect of the invention can be formulated to contain from 0.001 wt % to 50 wt % caffeine. In certain embodiments, the compositions are formulated to contain from about 0.001 to 500 mg caffeine, although the compositions may be formulated to deliver any desired amount of caffeine. The compositions may also include an inotropic agent to enhance muscle twitching, such as from 0.001 to 50 wt % of the composition. Permeation enhancers may also be included in the compositions.

Application of caffeine to at least one eyelid serves to reduce the oxidative stress within the treated and untreated eye, thus helping to maintain the health of the eye and prevent oxidative damage. In particular, application of caffeine to at least one eyelid aids in inhibiting the formation of cataracts. Moreover, application of caffeine to at least one eyelid of a individual suffering from cataract(s) reduces the growth of and/or slows the further growth of the cataract(s). Typically the caffeine-containing composition is applied to the eyelid of the affected eye(s), but because caffeine reaches both the treated and untreated eye, it is not necessary to apply directly to the eyelid of the affected eye.

Ophthalmic Compositions in General: Ophthalmic compositions of the invention can be formulated to contain therapeutic agent or drug(s) for the treatment of watery eyes or epiphora, that can, for example, be due to overactive tearing reflex (from dry eye, for example), keratitis, photophobia, allergic conjunctivitis or nasolacrimal duct obstruction including pharmaceutically effective amounts of atropine, scopolamine, homoatropine, cyclopentalate, tropicamide and the like and anticholinergic agents such as combinations thereof. Allergic eye disease generally involves an allergic reaction of the ocular mucosa and the conjuntiva. Seasonal keratoconjucntivitis, perennial allergic conjunctivitis, vernal keratoconjuntivitis and atopic conjunctivitis are successfully treated with the compositions, kits and methods of the invention. Meibomian glandular dysfunction, blepharitis, rosacea, chalazion, and hordeolum may be treated according to the methods of the invention by topical application to at least one eyelid of a composition of the invention containing one or more cholinergic agents, antiinflammatory drug, or antibiotic. The therapeutic agents that may be included include pilocarpine, cyclosporine A, carbachol, echothiophate iodide, diisopropyl fluorophosphates, physostigmine, neostigmine, dipivefrin, apraclonodine, isoproternol, bromocriptine or phenylepherine, and antibiotics such as the tetracycline class, aminoglycosides, cephalosporins, antifungals (e.g., Neomycin and Polymixin) and the like appropriate for the condition to be treated, and optionally, up to about 50% of a micro fasciculating agent, such as caffeine, theophyline or theobromine, for example. Generally, the drug targets the meibomian glands to improve the lipid layer of the tear film, which improves tear stability, decreases evaporation and improves tear spread.

Traditionally, treatment of dry eye, dry mouth (Sjögren's Syndrome) or blepharitis, for example, has included oral administration (systemic delivery) of the appropriate therapeutic agent, such as the secretogues, pilocarpine, pilocarpine extract or tincture and physostigmine, which are indicated for dry eye and dry mouth and antibiotics such as oxytetracycline have been orally administered for the treatment of blepharitis. Unfortunately, systemic cholinergic stimulation is accompanied by numerous unwanted side effects including sweating, bracycardia, hypotension, nausea, vomiting and increased urination, while antibiotics are simply not tolerated by many people.

The compositions and methods of the present invention enable topical administration of drugs such as secretogues, e.g., pilocarpine (which is a muscarinic receptor agonist as well as a cholinergic agent) and physostigmine, alone or in combination with a micro fasciculating agent, directly to the eyelid (one or both eyelids) with or without the use of vasoconstrictors, for delivery to the target site, e.g., the lacrimal glands, meibomian glands, conjuctival goblet cells, resulting in secretions from all three layers of tear film. Similarly, anti-inflammatories, such as cyclosporine (molecular weight 1202 Daltons), which is typically applied to dry eye via eye drops that cause a stinging sensation in up to 20 to 30% of patients and require months to achieve varying degrees of efficacy, may be applied via the present methods, thus avoiding unpleasant side effects and resulting in delivery of the drug through the eyelid to the accessory lacrimal, lacrimal, and conjuntival mucosa and meibomian glands, thus achieving therapeutic effect in less time than previously observed.

The methods and compositions of the present invention may be applied to the treatment of various ophthalmic conditions and diseases including blepharitis, floppy eyelid syndrome, trachomatous dry eye, retinopathy, retinal degeneration, nasolacrimal duct obstruction, epiphora, chalazion, hordeolum, allergic conjunctivitis and keratitis, infectious conjunctivitis and keratitis, pterygium, pinguiculum, iritis, uveitis, keratitis, vitritis, vitreous floaters, vitreous detachment, vitreous hemorrhage, retinal detachment, sub retinal hemorrhage, choridal neovascular membrane, retinal edema, macular edema, diabetic retinopathy, choridal malignancy, orbital malignancy, eyelid tumors, optic neuritis, optic neuropathy, strabismus, refractive error, and glaucoma. The ophthalmic compositions of the invention used to treat these various conditions and diseases comprise the appropriate active ingredient for treatment, such as anti-inflammatory agents (steroidal anti-inflammatory agents such as prednisone, triamcinolone, dexamethasone, Durezol, Fluorometholone, loteprendol, and the like; non-steroidal anti-inflammatory drugs (NSAIDs) such as ketorolac, bromphenac, nephenac, and the like, and immunosuppressive agents, such as: cyclosporine, tacrilimus, sirolimus, and the like); Dry Eye Syndrome Agents such as cholinergics which include (a) muscarinic receptor agonists (Pilocarpine, Cevimeline, Carbachol), (b) anticholinesterase agents: physostigmine, neostigmine, echothiophate iodide, pyridostigmine, edrophonium; Beta-agonists such as Isoproternol; Alpha-agonists (e.g., brimonidine, iopidine, epinepherine, phenylepherine, all vasoconstrictors; tetracycline class antibiotics (e.g., for Rosecea) such as doxycycline, tetracycline; estrogens and androgens; and immunosupressives such as cyclosporine, and the like; Antiglaucoma agents such as Betaantagonists, Alpha-antagonists, carbonic anhydrase inhibitors, prostaglandin analogs (e.g., in certain embodiments, a skin bleaching agent or anti melanocytic agent may be added to the compositions to prevent skin darkening (e.g., hydroquinone), anticholinergic compounds (including muscarinic receptor agonists), vasodilators. Possible glaucoma drug combinations include B-antagonist and alpha-antagonist, B-antagonist and carbonic anhydrase inhibitor, B-antagonist and prostaglandin analog, anticholinergic (including muscarinic agonists) and alpha-agonist, any Intraocular pressure lowering agent and vasodilator, any intraocular pressure lowering agent and neuroprotective agent; antibiotics such as Cephalosporins, Fluoroquinolone(ciprofloxacin, moxifloxacin, gatifloxacin), Macrolide(erythromycin, azithromycin, etc), Tetracycline class, Aminoglycosides(Tobramycin, gentamycin), Trimethoprim, Sulfonamides, and the like; Antihistamines such as emedastine, levocabastine, antazoline, pheniramine, azelastine, and the like; mast cell stabilizers such as lodoxamide, olopatadine, Ketotifen, Cromolyn Sodium and the like; ocular decongestants such as Naphazoline, Phenylepherine, Tetrahydrozoline, Oxymetazoline, and the like; Anti-VEGF (vascular endothelial growth factorsuch as Lucentis ranibizumab and Avastin (bevacizumab); Anti EGFI (epidermal growth factor inhibitor) Erlotinib(Tarceva), Gefitinib(Iressa); Neuroprotective agents such as Memantine(Namenda), Cholesterol lowering Medications including statins, IOP lowering agents that are also neuroprotective(Brimonidine(Alphagan), Betaxolol(Betoptic); herbal agents, including various extracts, ginko biloba, and the like; vitamins, minerals, and the like; and oligonucleotides.

In another aspect of the invention, compositions comprising a therapeutically effective amount of a desired therapeutic agent or combination of therapeutic agents and from about 0.001 to 50 wt % muscle fasciculating agent are formulated for topical transdermal administration. In this aspect of the invention, the composition is administered to any outer skin surface of a patient. Any drug or therapeutic agent that can be applied transdermally can be used in combination with a muscle fasciculating agent and optional ionotropic agent as described herein and formulated in any convenient form for topical administrations, such as a lotion, crème, patch, and the like. In certain embodiments the composition further comprises a permeability enhancer. In certain embodiments of this aspect of the invention, the muscle fasciculating agent is caffeine, theophylline, pentoxifyline or theobromide, which may be included in the topical composition in an amount of up to about 1% and in certain embodiments may be included in an amount of up to about 30 wt % or in certain other embodiments, up to about 50 wt % of the composition. In certain embodiments of this aspect of the invention the drug(s) is less than 6000 Daltons in size, while in other embodiments the drug may be larger than 6000 Daltons in size. Non-limiting examples of drugs that may be included in the compositions for topical transdermal delivery include insulin, recombinant insulin, botox, myobloc, antihypertensive agents, nicotine, antibiotics, hormones, recombinant hormones, and anti-arrhythmic agents. The muscle fasciculating agent serves to stimulate subcutaneous muscle, which serves to increase absorption of the active agent into muscle. An optional ionotropic agent serves to enhance the muscle contractions, further enhancing absorption of the drug. Since muscle is highly vascular, increasing absorption into muscle results in increased absorption of the drug into the body.

Optionally, an amount of a penetrating agent may also be included in any of the compositions of the invention to aid penetration of the active component into and across the skin or eyelid skin such as for example, aliphatic alcohol, fatty acid and a salt thereof, fatty acid ester, polyalcohol alkyl ether, polyoxyethylene alkyl ether, glyceride, polyalcohol medium chain fatty acid ester, polyoxyethylene sorbitan fatty acid ester, alkyl lactate ester, terpenes and organic amine. More specifically, the percutaeous penetrating agent may be ethanol, glycerol, diethylene glycol, propylene glycol, polyethylene glycol and higher aliphatic alcohols (saturated or unsaturated higher aliphatic alcohol having 12 to 22 carbon atoms such as oleyl alcohol, lauryl alcohol and stearyl alcohol), capric acid, myristic acid, palmitic acid, lauric acid, stearic acid, isostearic acid, oleic acid, linoleic acid and linolenic acid, and a salt thereof (for example, sodium salt, potassium salt, magnesium salt, calcium salt and aluminium salt), include an ester of a fatty acid such as myristic acid, palmitic acid, lauric acid, stearic acid, isostearic acid, oleic acid, linoleic acid, linolenic acid, propionic acid, butyric acid, isobutyric acid, valeric acid, pivalic acid, caproic acid, heptanoic acid, malonic acid, succinic acid, glutaric acid, adipic acid, pimelic acid, crotonic acid, sorbic acid, maleic acid, fumaric acid and sebacic acid with a lower aliphatic alcohol such as methanol, ethanol, propanol, isopropanol, butanol, pentanol, hexanol, heptanol and octanol, isopropyl myristate, isopropyl palmitate, diisopropyl adipate and diethyl sebacate, an ether of a polyalcohol such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, methyl glucoside, oligosaccharide and reduced oligosaccharide with alkyl alcohol, polyoxyethylene lauryl ether, polyoxyethylene cetyl ether, polyoxyethylene stearyl ether and polyoxyethylene oleyl ether, glycerol ester of fatty acid having 6 to 18 carbon atoms (e.g;, monoglyceride, diglyceride, triglyceride and a mixture thereof), glyceryl monolaurate, glyceryl monomyristate, glyceryl monostearate, glyceryl monooleate, glyceryl dilaurate, glyceryl dimyristate, glyceryl distearate, glyceryl trilaurate, glyceryl trimyristate and glyceryl tristearate, ethylene glycol monocaprylate, propylene glycol monocaprylate, glycerin monocaprylate, mono 2-ethylene glycol ethylhexanoate, mono 2-propylene glycol ethylhexanoate, di(2-propylene)glycol ethylhexanoate, propylene glycol, dicaprylate, polyoxyethylene sorbitan monolaurate, polyoxyethylene sorbitan monostearate and polyoxyethylene sorbitan monooleate, methyl lactate, ethyl lactate, methyl 2-methoxy propionate and ethyl 2-methoxypropionate, monoethanolamine, triethanolamine, creatinine and meglumine. In certain embodiments of the invention one or more of fatty acid ester, polyoxyethylene, isopropyl myristate and polyoxyethylene oleyl ether is included in the composition. In other embodiments of the invention a penetrating agent or combination of agents such as 1-acyl-azacycloheptan-2-one (azone), 1-acyl-glucoside, 1-acyl-poly(oxyethylene), 1-acyl-saccharide, 2-(n-acyl)-cyclohexanone, 1-alkanol, 1-alkanoic acid, 2-(n-acyl)-1,3-doxolane (SEPA), 1,2,3-triacylglyceride, 1-alkylacetate, alkyl-sulfate, dialkyl sulfate, and phenyl-alkyl-amine may be added to the composition.

Also optionally, an amount of a hydrating agent such as hyaluronic acid, saline solution, polyvinylpyrrolidone, may be included in any of the compositions of the invention. Ophthalmic compositions of the invention that are intended to penetrate the stratum corneum generally, although not necessarily, include an amount of a hydrating agent to facilitate penetration of the therapeutic agent through the cell junctions of the stratum corneum.

When included in the compositions of the invention, penetrating agents are generally in the amount of from 0.01% to 50% by weight of the composition and in some embodiments from 0.1% to about 40% by weight of the composition, 1% to about 35% and in other embodiments from about 5% to about 30% by weight of the composition and the amount of hydrating agent is in the range of from 0.001% to 30% by weight of the composition, in other embodiments from 0.01 to 25% by weight of the composition and in still other embodiments, from 0.1% to 10% by weight of the composition.

The compositions of the invention may be formulated as a cream, gel, lotion, ointment, stick, spray, foam, film, strip, tape, poultice, plaster, adhesive preparation or the like for direct application to the skin or to the outer surface of the upper eyelid or may be adhered to a patch, strip, tape, poultice, plaster and the like that is suitable for application to the skin or to the outer surface of the upper eyelid. Because drug delivery through the eyelid is so effective, the compositions for application to the eyelid can be formulated to contain less drug or therapeutic agent than is routinely administered via eye drops or for systemic delivery (e.g., via injection, oral dosage, and the like) to treat the condition via topical application. Moreover, because the composition for application to the outer surface of the eyelid is not applied directly to the eye, the pH of these formulations of the invention can range from 0 to 14, enabling the use of a wide range of therapeutic agents that ordinarily cannot be formulated for topical application to the eye. Also, because there is little or no limitation on the pH of the compositions of the invention, pH can be manipulated to maximize penetration of drug through the eyelid. By manipulating pH of the composition, it is possible to maximize penetration of unbound therapeutic agent through the skin.

In addition to the components discussed above, any component generally used for manufacturing medicine in the desired form can be added to the present compositions of the invention, if desired. Examples of such components include a base matrix for adhesive preparations, an ointment base, gel base, solvent, oil, crosslinking agent, surfactant, gum, resin, pH adjuster, stabilizer, antioxidant, preservative, ultraviolet absorbent and wetting agent. A percutaneous absorption enhancer can be added, if desired.

The base matrix for an adhesive preparation may include an acrylic pressure sensitive adhesive, a silicone pressure sensitive adhesive and/or rubber pressure sensitive adhesive, for example. The matrix can be retained on one surface of a support generally used in a preparation to be applied to the skin surface such as tape, patch, cataplasma and plaster, or on one surface of a support composed of any material having no adverse effect on the present invention.

An acrylic pressure sensitive adhesive may include acrylic acid-octyl acrylate copolymer, acrylate-vinyl acetate copolymer, 2-ethylhexyl acrylate-vinyl pyrrolidone copolymer and/or methacrylic acid-butyl acrylate copolymer. Silicone pressure sensitive adhesives useful in certain embodiments of the invention include polymethylphenylsiloxane copolymer and/or acrylic acid-dimethylsiloxane copolymer, for example. Rubber pressure sensitive adhesives that may be used in certain embodiments of the invention include for example styrene-isoprene-styrene copolymer, natural rubber, polyisobutylene, polybutene and/or ethylene-vinyl acetate copolymer (EVA), to which tackifier resin, softener and the like can be added, if desired.

Ointment based formulations may include fat and oil bases such as Vaseline®, paraffin, plastibase, silicone, vegetable oil, lard, wax and unguentum simplex; and/or emulsion bases such as hydrophilic ointment (vanishing cream), hydrophilic Vaseline®, absorption ointment, hydrous lanolin, purified lanolin and hydrophilic plastibase (cold cream).

Gel based formulations may include thickening polymers such as carboxyvinyl polymer, polyacrylic acid, sodium polyacrylate, methylcellulose, polyvinyl alcohol, polyvinyl pyrrolidone, polyethylene oxide, polyacrylamide, gelatine, acacia gum, tragacanth, guar gum, xanthan gum, agar, chitosan and carageenan; fatty acid esters such as isopropyl myristate, isopropyl palmitate and propylene glycol oleate; fatty acids such as lactic acid, lauric acid, oleic acid, linoleic acid and linolenic acid; aliphatic alcohols such as lauryl alcohol and oleyl alcohol; and hydrocarbons such as squalene and squalane.

Solvents used in the manufacture of the compositions of the invention may include purified water, methanol, ethanol, 1-propanol, lower alcohol, ethyl acetate, diethyl ether, tert-butylmethyl ether, pyrrolidone, acetic acid, acetonitrile, N,N-dimethylformamide, acetone, methyl ethyl ketone, methyl isobutyl ketone, tetrahydrofuran, chloroform, toluene and xylene, and the like.

Oils used in the manufacture of the compositions of the invention may include volatile or involatile oil, solvent and resin. Oil is generally used in an external preparation for skin and may be in a liquid, paste or solid form at room temperature. Specifically, for example, higher alcohols such as cetyl alcohol and isostearyl alcohol; fatty acids such as isostearic acid and oleic acid; polyalcohols such as glycerol, sorbitol, ethylene glycol, propylene glycol and polyethylene glycol; and esters such as myristyl myristate, hexyl laurate, decyl oleate, isopropyl myristate and glyceryl monostearate can be mentioned.

When included, a crosslinking agent may be for example a polyisocyanate, organic peroxide, organometallic salt, alkoxide and metal chelate, examples of which are well known in the art of manufacturing topical medications for use in humans.

Surfactant may be included in the compositions of the invention to facilitate dissolution of formulation components and/or absorption, including anionic surfactant, cationic surfactant, nonionic surfactant and amphoteric surfactant. Useful surfactants include fatty acid salt, alkyl sulfate, polyoxyethylene alkyl sulfate, alkyl sulfo carboxylate, alkyl ether carboxylate, amine salt, quanternary ammonium salt, polysorbate 80, polyoxyethylene hydrogenated castor oil, polyoxyethylene fatty acid ester, polyoxyethylene alkyl ether, polyoxyethylene sorbitan fatty acid ester, alkyl betaine, dimethylalkylglycine and lecithin.

If desired, gum and/or resin may be included in the compositions of the invention, including for example, sodium polyacrylate, cellulose ether, calcium alginate, carboxyvinyl polymer, ethylene-acrylic acid copolymer, vinyl pyrrolidone polymer, vinyl alcohol-vinyl pyrrolidone copolymer, nitrogen-substituted acrylamide polymer, polyacrylamide, cationic polymer such as cationic guar gum, dimethylacrylic ammonium polymer, acrylic acid-methacrylic acid copolymer, polyoxyethylene-polypropylene copolymer, polyvinyl alcohol, pullulan, agar, gelatine, chitosan, polysaccharide from tamarindo seed, xanthan gum, carageenan, high-methoxyl pectin, low-methoxyl pectin, guar gum, acacia gum, microcrystalline cellulose, arabinogalactan, karaya gum, tragacanth gum, alginate, albumin, casein, curdlan, gellan gum, dextran, cellulose, polyethyleneimine, high polymerized polyethylene glycol, cationic silicone polymer, synthetic latex, acrylic silicone, trimethylsiloxysilicate and fluorinated silicone resin.

A pH adjuster may be used in the compositions to adjust pH of the composition to a desired range, such as pH 4-10, or pH 5-8, for example or any range that maximizes the penetration through the skin of the particular drug in the composition. pH adjustment can be achieved through use of various chemicals such as hydrochloric acid, citric acid, sodium citrate, acetic acid, sodium acetate, ammonium acetate, succinic acid, tartaric acid, L-sodium tartrate, sodium hydrate, potassium hydrate, sodium carbonate, sodium hydrogencarbonate, lactic acid, calcium lactate, sodium lactate, sodium fumarate, sodium propionate, boric acid, ammonium borate, maleic acid, phosphoric acid, sodium hydrogenphosphate, dl-malic acid, adipic acid, triethanolamine, diisopropanolamine, meglumine, monoethanolamine, sulfuric acid and aluminum potassium sulfate and the like.

Stabilizers may optionally be included in the compositions of the invention. Useful stabilizers include for example sodium bisulfite, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl palmitate, dl-.alpha.-tocopherol, nordihydroguaiaretic acid, 1-hydroxyethylidene-1,1-diphosphonic acid, disodium edetate, tetrasodium edetate dehydrate, sodium citrate, sodium polyphosphate, sodium metaphosphate, gluconic acid, phosphoric acid, citric acid, ascorbic acid and/or succinic acid.

Other optional components of the compositions include wetting agents such as glycerol, polyethylene glycol, sorbitol, maltitol, propylene-glycol, 1,3-butanediol and hydrogenated maltose syrup; antioxidants such as sodium bisulfite, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl, palmitate, dl-.alpha.-tocopherol and nordihydroguaiaretic acid; preservatives such as methylparaben, propylparaben, chlorobutanol, benzyl alcohol, phenylethyl alcohol, benzalkonium chloride, phenol, cresol, thimerosal, dehydroacetic acid and sorbic acid; ultraviolet absorbent such as octyl methoxycinnamate, glyceryl monooctanoate di-para-methoxy cinnamate, 2-hydroxy-4-methoxybenzophenone, para-aminobenzoic acid, para-aminobenzoic acid glycerol ester, N,N-dipropoxy-para-aminobenzoic acid ethyl ester, N,N-diethoxy-para-aminobenzoic acid ethyl ester, N,N-dimethyl-para-aminobenzoic aid ethyl ester, N,N-dimethyl-para-aminobenzoic acid butyl ester, homomethyl N-acetylanthranilate, amyl salicylate, menthyl salicylate, homomethyl salicylate, octyl salicylate, phenyl salicylate, benzyl salicylate and p-isopropyl phenyl salicylate.

The formulations of the invention may be in any form, e.g., gels, creams, lotions, and the like. The formulations are not limited in form and may include for example liposomes and other vesicles, such as transfersomes, which include surface active agents and are particularly useful for the transdermal delivery of large molecules such as peptide and proteins; and thosomes, which are liposomes that contain ethanol, which functions as a permeation enhancer.

The following tables provide non-limiting examples of excipients (and amounts thereof) that may be included in the inventive compositions.

Gel Formulations:

| Class | Excipients |
| --- | --- |
| Polymers | Methyl cellulose |
| | Hydroxyethylcellulose |
| | Hydropropylcellulose |
| | Hydroxypropylmethyl cellulose |
| | Sodium carboxy methyl cellulose |
| | Carbopol |
| | Chitosan |
| | Poloxamer (Pluronics ®) |
| | Sodium alginate |
| | Polyvinyl alcohol |
| | Xanthan gum |

Cream Formulations:

| Class | Excipient |
| --- | --- |
| Hydrophobic excipients | Stearic acid |
| | Palmitic acid |
| | Lauric acid |
| | Capric acid |
| | Mineral oil |
| | Bees wax |
| | Silicone oil |
| Emulsifiers (Hydrophobic and Hydrophilic) | Stearyl alcohol |
| | Cetyl alcohol |
| | Glyceryl monostearate |
| | Polyethylene glycol monostearate |
| | Sorbitan monostearate |
| | Sorbitan monolaurate |
| | Sorbitan monopalmitate |
| | Sorbitan monostearate |
| | Sorbitan monoleate |
| | Sorbitan sesquiolate |
| | Sorbitan trioleate |
| | Cetaryl alcohol |
| | Cetereth 20 (ethoxylated derivative of cetaryl alcohol) |
| | Sodium stearoyl-2-lactylate |
| | Calcium stearoyl-2 lactylate |
| | Polysorbate |
| | Sodium lauryl sulfate |
| | Stearyl colamino formyl methyl pyridinium chloride |
| | Sodium borate |
| | Polyoxyethylene lauryl alcohol |
| | Polyoxylated oleyl alcohol |
| | Polyoxyethylene stearate |
| | Polyoxyethylene sorbitan monostearate |
| | Polyoxyethylene glycol monostearate |
| | Propylene glycol monostearate |
| | Ethoxylated lanolin |
| | Ethoxylated cholesterol |
| Hydrophilic excipients | Purified water |
| | Buffers |
| | Polymers (as outlined for gels) |

| Class | Excipient |
|---|---|
| Humectants | Glycerin |
| | Sorbitol |
| | Propylene glycol |
| | Polyethylene glycol (low molecular weight) |

Ointment Formulations:
Petrolatum
White wax
Lanolin
Mineral oil
Bees wax
Microcrystalline wax
Cholesterol
Cetyl alcohol
Stearyl alcohol
Sorbitan sesquioleate
Lanolin alcohol Exemplary Preservatives that May be Included in the Compositions of the Invention:

| Preservatives | Bithional |
|---|---|
| | Butyl p-hydroxybenzoate |
| | p-chloro-m-xylenol |
| | Dehydroacetic acid |
| | Ethyl paraben |
| | Methyl-p-hydroxybenzoate |
| | Propyl-p-hydroxybenzoate |
| | Sorbic acid |

Exemplary Hydrating Agents that May be Included in the Compositions of the Invention and Exemplified Amounts Thereof:

| Excipient | FDA Maximum Potency |
|---|---|
| LACTIC ACID | TOPICAL; EMULSION, CREAM: 1.00% |
| | TOPICAL GEL: 6.07% |
| SORBITOL | TOPICAL LOTION: 5.70% |
| | TOPICAL OINTMENT: NOT KNOWN |
| | TOPICAL SUSPENSION: 0.70% |
| | TOPICAL SOLUTION: 18.06% |
| | TOPICAL; EMULSION: 7.00% |
| | TOPICAL; EMULSION, CREAM: 67.52% |
| | TOPICAL; LOTION: NOT KNOWN |
| GLYCERIN | TOPICAL; CREAM: 4.0% |
| | TOPICAL; CREAM, EMULSION,: 2.0% |
| | TOPICAL; EMULSION, CREAM: 20.0% |
| | TOPICAL; GEL: 20.0% |
| | TOPICAL; LOTION: 50.0% |
| | TOPICAL; OINTMENT: NOT KNOWN |
| | TOPICAL; SOLUTION: 50.0% |
| | TRANSDERMAL; GEL: 5.0% |
| HEXANETRIOL (1,2,6-HEXANETRIOL) | TOPICAL; EMULSION, CREAM: 7.50% |
| PROPYLENE GLYCOL | TRANSDERMAL GEL: 6.0% |
| | TOPICAL OINTMENT: 38% |
| | TOPICAL LOTION: 59% |
| | TOPICAL GEL: 98.09% |
| | TOPICAL EMULSION CREAM: 71.08% |
| HEXYLENE GLYCOL | TOPICAL; EMULSION, CREAM: 12.0% |
| | TOPICAL; GEL: 2.0% |
| | TOPICAL; OINTMENT: 12.0% |
| | TOPICAL; SOLUTION: 12.0% |
| POLYETHYLENE GLYCOL 200 | TOPICAL; SOLUTION: 29.70% |
| | TOPICAL; OINTMENT: 39.0% |
| POLYETHYLENE GLYCOL 300 | TOPICAL; OINTMENT: 57.0% |
| | TOPICAL; SOLUTION: 29.70% |
| POLYETHYLENE GLYCOL 400 | TOPICAL; EMULSION, CREAM: 7.50% |
| | TOPICAL; GEL: 45.0% |
| | TOPICAL; LOTION: 12.0% |
| | TOPICAL; OINTMENT: 65.0% |
| | TOPICAL; SOLUTION: 69.90% |

Examples of Other Useful Hydrating Agents:
Glycolic Acid
Glycolate salts
D-panthenol
Hyaluronic acid
Lactamide monoethanolamine
Acetamide monoethanolamine Exemplary Permeation Enhancers for Use in the Compositions of the Invention (and Exemplified Amounts Thereof):

| Class | Excipient | FDA Maximum Potency |
|---|---|---|
| Terpenes | MENTHOL | TOPICAL LOTION: 0.05% |
| | LIMONENE, DL- | TOPICAL SOLUTION: 0.08% |
| | A-TERPINEOL | TOPICAL LOTION: 10% |
| | | TOPICAL LOTION: 11% |
| Essential Oils | PEPPERMINT OIL | TOPICAL OINTMENT: NOT KNOWN |
| Fatty Acids and Esters | ISOPROPYL MYRISTATE | 0.02%-35% |
| | ISOPROPYL PALMITATE | 1.8%-3.9% |
| | OLEIC ACID | TOPICAL SOLUTION: 7.4% |
| | OLEYL OLEATE | TOPICAL OINTMENT: 2.55% |
| | STEARIC ACID | TOPICAL; CREAM, AUGMENTED: 3.0% |
| | | TOPICAL; EMULSION, CREAM: 22.60% |
| | | TOPICAL; LOTION: 20.0% |
| | | TOPICAL; OINTMENT: 15.0% |
| | | TOPICAL; SUSPENSION: 1.75% |

-continued

| Class | Excipient | FDA Maximum Potency |
|---|---|---|
| Alcohols, Glycols and glycerides | ETHYL ACETATE | TOPICAL; SOLUTION: 31.0% |
| | DIETHYL SEBACATE | TOPICAL; SOLUTION: 24.0% |
| | ALCOHOL | 1.20-97.50% |
| | PROPYLENE GLYCOL | TRANSDERMAL GEL: 6.0% |
| | | TOPICAL OINTMENT: 38% |
| | | TOPICAL OINTMENT AUGMENTED: 65.0% |
| | | TOPICAL LOTION: 59% |
| | | TOPICAL LOTION AUGMENTED: 30.0% |
| | | TOPICAL GEL: 98.09% |
| | | TOPICAL EMULSION CREAM: 71.08% |
| | | TOPICAL EMULSION LOTION: 47.50% |
| | BENZYL ALCOHOL | TOPICAL; CREAM, AUGMENTED: 1.00% |
| | | TOPICAL; CREAM, EMULSION, SUSTAINED RELEASE: 1.0% |
| | | TOPICAL; EMULSION, CREAM: 2.70% |
| | | TOPICAL; GEL: 50.0% |
| | | TOPICAL; LOTION: 1.30% |
| | | TOPICAL; OINTMENT: 2.20% |
| | | TOPICAL; SOLUTION: 2.0% |
| | | TOPICAL; SUSPENSION: 1.0% |
| | CAPRYLIC/CAPRIC TRIGLYCERIDE | TOPICAL; CREAM, EMULSION, SUSTAINED RELEASE: PENDING (10.0%) |
| | | TOPICAL; EMULSION, CREAM: PENDING (10.80%) |
| | | TOPICAL; SOLUTION: PENDING (50.0%) |
| | CAPRYLIC/CAPRIC/STEARIC TRIGLYCERIDE | TOPICAL; OINTMENT: 70.0% |
| | MYRISTYL ALCOHOL | TOPICAL; EMULSION, CREAM: 3.0% |
| | | TOPICAL; LOTION: 1.0% |
| | | TOPICAL; SUSPENSION: 1.05% |
| | CETYL ALCOHOL | TOPICAL; CREAM, AUGMENTED: 4.0% |
| | | TOPICAL; CREAM, EMULSION, SUSTAINED RELEASE: 6.0% |
| | | TOPICAL; EMULSION, AEROSOL FOAM: 3.22% |
| | | TOPICAL; EMULSION, CREAM: 12.0% |
| | | TOPICAL; LOTION: 68.40% |
| | | TOPICAL; OINTMENT: 7.0% |
| | | TOPICAL; SUSPENSION: 2.01% |
| | CETOSTEARYL ALCOHOL | TOPICAL; CREAM, AUGMENTED: 8.0% |
| | | TOPICAL; EMULSION, CREAM: 12.0% |
| | | TOPICAL; EMULSION, LOTION: 5.0% |
| | | TOPICAL; LOTION: 4.0% |
| | | TOPICAL; OINTMENT: 1.20% |
| | | TOPICAL; SUSPENSION: 2.50% |
| | STEARYL ALCOHOL | TOPICAL; AEROSOL: 0.53% |
| | | TOPICAL; CREAM, AUGMENTED: 4.0% |
| | | TOPICAL; CREAM, EMULSION, SUSTAINED RELEASE: 3.0% |
| | | TOPICAL; EMULSION, AEROSOL FOAM: 0.53% |
| | | TOPICAL; EMULSION, CREAM: 30.0% |
| | | TOPICAL; LOTION: 12.0% |
| | | TOPICAL; OINTMENT: 8.0% |
| | | TOPICAL; SUSPENSION: 2.01% |
| | | VAGINAL; EMULSION, CREAM: 42.50% |
| | | TOPICAL; OINTMENT: PENDING (0.75%) |

-continued

| Class | Excipient | FDA Maximum Potency |
|---|---|---|
| | OLEYL ALCOHOL | TOPICAL; EMULSION, CREAM: 10.0% |
| | | TOPICAL; OINTMENT: 5.0% |
| Surfactants | SODIUM LAURYL SULFATE | TOPICAL; EMULSION, CREAM: 2.50% |
| | | TOPICAL; LOTION: 0.50% |
| | | TOPICAL; OINTMENT: 1.0% |
| | POLYSORBATE 20 | TOPICAL; EMULSION: 2.0% |
| | | TOPICAL; EMULSION, CREAM: 0.80% |
| | | TOPICAL; LOTION: 7.8% |
| | | TOPICAL; SOLUTION: 15.0% |
| | POLYSORBATE 60 | TOPICAL; EMULSION, AEROSOL FOAM: 0.42% |
| | | TOPICAL; EMULSION, CREAM: 8.0% |
| | | TOPICAL; LOTION: 5.0% |
| | | TOPICAL; SHAMPOO: 15.0% |
| | | TOPICAL; SUSPENSION: 2.85% |
| | LECITHIN | TOPICAL; GEL: 1.0% |
| | | TOPICAL; SOLUTION: 1.40% |

Other Permeation Enhancers

| Class | Excipient |
|---|---|
| Terpenes | Eucalyptol: 1,8-cineole |
| | α-pinene |
| | Menthone |
| | Nerolidol |
| | Terpineol |
| | Carvol |
| | Carvone |
| | Pulegone |
| | cyclohexane oxide |
| | limonene oxide |
| | Anise |
| Essential Oils | Eucalyptus |
| | turpentine oil |
| Amides | Urea |
| | Dimethylacetamide (DMA) |
| | Diethyltoluamide |
| | dimethylformamide (DMF) |
| | Dimethyloctamide |
| | Dimethyldecamide |
| | N-methyl-2-pyrrolidone (NMP) |
| | 2-pyrrolidone |
| | N-dodceyl-2-pyrrolidone (2-pyrrolidone derivative) |
| | Fatty acid esters of N-(2-hydroxyethyl)-2-pyrrolidone (HEP) |
| | 1-butyl-3-dodecyl-2-pyrrolidone |
| | 1-ethyl-2-pyrrolidone |
| | 1-butyl-2-pyrrolidone |
| | 1-hexyl-2-pyrrolidone |
| | 1-octyl-2-pyrrolidone |
| | 1-lauryl-2-pyrrolidone |
| | 1-methyl-4-carboxy-2-pyrrolidone |
| | 1-hexyl-4-carboxy-2-pyrrolidone |
| | 1-lauryl-4-carboxy-2-pyrrolidone |
| | 1-methyl-4-methoxycarbonyl-2-pyrrolidone |
| | 1-hexyl-4-methoxycarbonyl-2-pyrrolidone |
| | 1-lauryl-4-methoxycarbonyl-2-pyrrolidone |
| | N-cyclohexylpyrrolidone |
| | N-dimethylaminopropyl-pyrrolidone |
| | N-cocoalkypyrrolidone |
| | n-tallowalkylpyrrolidone |
| Fatty Acids and Esters | Linoleic Acid |
| | Sodium Oleate |
| | Lauric Acid |
| | Capric Acid |
| | Neodecanoic acid |
| | Fatty acid extract of cod liver oil |
| | Valeric |
| | Heptanoic |
| | Pelagonic |
| | caproic |
| | capric |
| | caprylic |
| | palmitoleic acid |
| | Isovaleric |
| | Neopentanoic |
| | Neoheptanoic |
| | Neononanoic |
| | trimethyl hexanoic |
| | Neodecanoic |
| | Isostearic |
| | isopropyl n-butyrate |
| | isopropyl n-hexanoate |
| | isopropyl n-decanoate |
| | isopropyl myristate |
| | isopropyl palmitate |
| | octyldodecyl myristate |
| | ethyl acetate |
| | butyl acetate |
| | methyl acetate |
| | Methylvalerate |
| | Methylpropionate |
| | diethyl sebacate |
| | ethyl oleate |
| Sulfoxides and Similar Compounds | Dimethyl sulfoxide (DMSO) |
| | Decylmethyl sulfoxide (DCMS) |
| | Various N,N-dimethylamides |
| | N,N-dimethylformamide |
| | Dimethylacetamide (DMA) |
| | N,N-dimethyloctanamide |
| | N,N-dimethyldecanamide |
| Alcohols, Glycols and Glycerides | n-alkanols (1-nonanol, octyl alcohol) |
| | Lauryl alcohol |
| | Propanol |
| | Butanol |
| | 2-butanol |
| | Pentanol |
| | 2-pentanol |
| | Hexanol |
| | Octanol |
| | Nonanol |
| | Decanol |
| | glycerol monocaprylate |
| | decyl alcohol |
| | Lauryl alcohol |
| | Linoleyl alcohol |
| | linolenyl alcohol |

| Class | Excipient |
|---|---|
| | ethylene glycol |
| | diethylene glycol |
| | triethylene glycol |
| | dipropylene glycol |
| | Propanediol |
| | Butanediol |
| | Pentanediol |
| Surfactants | Sodium laurate |
| | sodium octyl sulfate |
| | cetyltrimethylammonium bromide |
| | tetradecyltrimethylammonium bromide |
| | octyltrimethyl ammonium bromide |
| | benzalkonium chloride |
| | cetylpyridinium chloride |
| | dodecyltrimethylammonium chloride |
| | hexadecyltrimethylammonium chloride |
| | hexadecyl trimethyl ammoniopropane sulfonate |
| | oleyl betaine |
| | Cocamidopropyl Hydroxysultaine |
| | cocamidopropyl betaine |
| | Brij (30, 93, 96, 99) |
| | Span (20, 40, 60, 80, 85) |
| | Tween (20, 40, 60, 80) |
| | Myrj (45, 51, 52) |
| | Miglyol 840 |
| | sodium cholate |
| | sodium salts of taurocholic (TC) |
| | Glycolic |
| | desoxycholic acids |
| Phospholipids | phosphatidyl glycerol |
| | phosphatidyl glycerol derivatives (PGE, PGS, DMPG, DSPG, DOPG) |
| | phosphatidyl choline derviatives (PCS, PCE, DOPC, DLPC, HPC) |
| Cyclodextrin Complexes | β-cyclodextrin |
| | methyl-β-cyclodextrin |
| | O-carboxymethyl-o-ethyl-B-cyclodextrin (CME-B-CD) |
| | 2-hydroxypropyl-β-cyclodextrin (HPβCD) |
| | 2,6-dimethyl-β-cyclodextriin (DIMEB) |
| Amino Acid Derivatives | N-dodecyl-L-amino acid methyl ester |
| | n-pentyl-N-acetyl prolinate |
| | esters of omega amino acids (octyl-6-aminohexanoate and decyl-6-aminohexanoate) |
| Others | Clofibric Acid (amide and esters of) |
| | Enzymes (phopholipase C, triacylglycerol hydrolase (TGH, phospholipase A2 |

In certain embodiments of the invention where administration of more than one therapeutic agent or drug is desired, the different therapeutic agents or drugs can be separately applied to one or both upper eyelids (or to the same region of the skin in the case of transdedrmal application or to the same eye in the case of eye drops and the like for application to the underside of the eyelid(s)) or the different therapeutic agents or drugs may be applied to different eyelids (or different regions of the skin in the case of topical transdermal application or different eyes in the case of eye drops and the like for application to the underside of the eyelid(s)). In other embodiments of this aspect of the invention, one composition containing therapeutic agent or drug and up to 1 wt % or more of a muscle fasciculating agent and optional ingredients such as vasodilator, vasoconstrictor, permeating agent and combinations thereof is applied to the first eyelid of a human patient, while the second composition, which is applied to the other eyelid, does not contain a micro fasciculating agent and/or one or more optional component. For example, combination therapy for glaucoma or dry eye where two or more active agents are used to treat the condition may be carried out by applying one drug or set of drugs to one eyelid and another drug or combination of drugs to the other eyelid. Similarly, one therapeutic component such as a vasodilator may be applied to one eyelid and other active components and other components may be applied to the other eyelid. It is understood that the same treatments apply to eyedrops and the like that are applied to the eye and which have contact with the underside of the eyelid(s).

For delivery of certain drugs or therapeutic agents or for treatment of certain conditions or diseases it may be desirable to administer the composition of the invention via injection of a solution containing the desired drug or therapeutic agent directly into the underside of any portion of the eyelid, such as that portion of the eyelid in direct contact with the eye although contact with the eye is not necessary, rather than by topical application to the upper eyelid. This method of drug delivery is most useful for accessing the periocular space and tissues to (a) achieve a high loading dose of drug; and (b) overcome drug permeability due to drug characteristics such as high molecular weight, ionization, etc. and is less invasive to the patient than injecting under the conjunctiva around the eyeball. For example, a high dose of Triamcinolone (Kenalog) MW 434 Daltons, a long acting steroid, or Avastin, a large charged molecule MW 149,000 Daltons can be injected via this method in order to achieve high drug concentrations without the invasive injection into or adjacent to the eyeball which most patients find unappealing and traumatic. Also, a therapy regiment may be applied when warranted, which includes an initial injection of a composition of the invention into the underside of the eyelid, followed by application of a topical composition containing a therapeutically effective amount of the therapeutic agent(s) to at least one eyelid at appropriate time intervals, e.g., within 1 to 24 hours following the injection and once per day thereafter until the condition is effectively treated or controlled. Conditions that can be treated in this manner include but are not limited to keratitis inflammation such as iritis, bleeding conditions such as hyphema, vascular occlusions, retinal edema, age related macular degeneration, and diabetic retinopathy. This method can be also be used to deliver steroids or antibiotics to the eye for example.

In another embodiment of the invention, iontophoresis is employed to ensure faster and possibly more effective uptake of drug or therapeutic agent into the eyelid or skin and hence circulatory system. Use of iontophoresis to deliver a composition optionally containing a micro fasciculating agent and drug or therapeutic agent can result in faster uptake and sustained release of drug or therapeutic agent. In this aspect of the invention, the drug that is applied to the skin or upper eyelid surface via iontophoresis is charged, e.g., Avastin (bevacizumab) which is a large charged molecule of MW 149,000 which ensures that it can be driven across the eyelid skin via the low electrical current provided by the iontophoresis electrode.

Although the inventors do not wish to be bound by any theory, it is proposed that the present methods and compositions achieve sustained release of therapeutic agent from the discovery of the uniquely permeable and vascular skin of the human eyelid into the systemic blood flow as long as the therapeutic agent remains unbound within the skin layer of the upper eyelid. Further, in those compositions of the invention containing a muscle fasciculating agent, it is believed that continual microcontractions in the blink muscle of the eyelid and muscle surrounding the eyeball caused by the muscle fasciculating agent result in a continual pumping action moving the drug into the surrounding muscle and the vascular system, which in humans flows towards the eyeball rather than away (as in other mammals), which in turn, facilitates penetration of the drug into the posterior segments of the eye (e.g., lens, vitreous, cilliary body, pars plana and plicata, retina, optic nerve, choroid and sclera as well as into the vascular system in general. As a result of the pumping action achieved through the use of a muscle fasciculating agent, or in various combinations with vasodilators, vasoconstrictors, and/or manipulation of the pH of the compositions of the present invention, the present methods enable the use of lower concentrations of therapeutic agent in topical formulations to treat conditions in the eye previously treated by systemic, oral or other topical routes using higher concentrations of drug or therapeutic agent than required by the present methods. The present invention also enables reduced frequency of treatment, improved drug targeting, continuous drug delivery, patient convenience and ease of treatment and potentially enhanced therapeutic effects.

Similarly, when the composition is applied to the skin rather than to the outer surface or underside of the eyelid(s), continual microcontractions in the muscle surrounding the area to which the composition is applied caused by the muscle fasciculating agent result in a continual pumping action moving the drug into the surrounding muscle and the vascular system. By manipulating the amount of a micro fasciculating agent in the compositions of the invention, it is possible to direct the drug in therapeutically effective amounts to its proper target and in some cases to a target that previously has not been accessible by non-invasive means or in concentrations not previously obtained via topical administration. By utilizing the unique vascular and dermal characteristics of the upper eyelid and optionally, inclusion of a micro fasciculating agent in the compositions, it is possible to specifically target and deliver drugs that heretofore could not be topically administered to achieve therapeutic concentrations of drug at the target site, such as large molecules, e.g. certain anti-inflammatories and antibiotics, lipophilic molecules, hormones, immunosuppressive agents, chemotherapeutic agents, non-steroidal anti-inflammatory agents, and anti-allergy agents. Antibiotics such as tetracyclines and other drugs such as demarcarium bromide, physiostigmine, neostigmine, pyridostigimine, isofluorophate, diisopropylfluorophosphate, carbachol, dipivefrin, apraclonodne, isoproternol, bromocriptine, phenylephrine, and echothiophate iodide, are non-limiting examples of drugs that can be delivered via the compositions, kits and methods of the invention. The skilled practitioner will appreciate that any therapeutic agent or drug (or combination of agents/drugs), particularly those having a size range of 6000 Daltons or smaller may be included in the compositions and kits of the invention, although larger molecules may also be used, e.g., cyclosporine, botox and other large organic molecules, and administered according to the methods described herein to achieve therapeutic concentration at the desired target site. Nonlimiting examples of active agents that may be delivered by the methods and compositions of the invention include glaucoma agents such as Ophthalmic Beta-Blockers, Carbonic Anhydrase Inhibitors, Alpha-Agonists, Miotics, Prostaglandin analogs, Latanoprost; Brimatoprosost; Acetazolamide; Apralonidine; Betaxolol; Brimonidine; Brinzolamide; Carbachol; Carteolol; Dorzolamide; Dipivefrin; Epinephrine; Levobunolol; Metipranolol; Methazolamide; Pilocarpine; Timolol; and Travaprost; Dry Eye agents such as Cyclosporine; Allergy Agents; Antihistamines; Antihistamine/decongestants; Antihistamine/mast cell stabilizers; Corticosteroids; Decongestants; Homeopathics; Mast cell stabilizers; Non-steroidal anti-inflammatory drug such as Optivar/Azelastine; aphazoline; Oxymetazoline; Phenylephrine; Tetrahydrozoline; Emandine/Emedastine; Elestat/Epinastine; Pataday, Patanol/ Olopatadine; Levocabastine; Alomide/Lodoxamide; Cromolyn; Alaway/Zaditor/Ketotifen; Alocril/Nedocromil; Alamast/Pemirolast; Loratadine and Pseudoephedrine; antibiotics such as Ciprofloxacin; Gatifloxacin; Gentamicin; Levofloxacin; Moxifloxacin; Ofloxacin; Sulfacetamide; Tobramycin; steroids such as Dexamethasone; Fluorometholone; Loteprednol; Medrysone; Prednisolone; Rimexolone; andnon-steroidal anti-inflammatory agents such as Bromfenac; Diclofenac; Flurbiprofen; Ketorolac; and Nepafenac.

Topical administration of the compositions of the invention to the upper eyelid can be achieved by any known means such as for example, through the use of an applicator such as a patch containing the composition on its surface intended for contact with the upper eyelid; a rollerball applicator integrally connected to a container in which the invention composition is contained; an applicator strip or plaster comprising a composition of the invention on the surface to be applied to the eyelid; a pliable finger cot containing a composition of the invention as a blister positioned on the tip thereof; or an applicator for dipping into a solution of a composition of the invention, any of which may be provided in a kit for a patients' or physician's or other medical personnel's use.

Topical administration of the compositions of the invention to any region of the skin is achieved by any known means, for example, by application of a patch containing the composition on a portion of its surface that is applied to the skin, a cream or lotion, strip, roller ball and the like.

Kits containing a composition(s) of the invention may include single use dosage forms of the invention composition, or may include a vial containing multiple doses that are to be metered out by the patient or via the applicator itself. Further, kits may include formulations of different therapeutic agents for treatment of the applicable condition or disease, intended to be applied to different eyelids or areas of the skin and/or at different times during the treatment regimen. Kits will also include, when necessary, instructions for the appropriate dosing regimen.

EXAMPLES

Example 1

Treatment of Severe Dry Eye

Two human patients with preexisting symptomatic severe dry eye were treated as follows. The dry eye condition was assessed by the Schirmers tear test and corneal observations. Each subject received a single application of a lotion containing 1% of pilocarpine and 0.16% caffeine applied to the upper eyelid of the more severely affected eye by direct application of the lotion to the upper eyelid. The effect of treatment was then measured over six hours in regards to tear production and comfort level of the patient.

Figure 2:
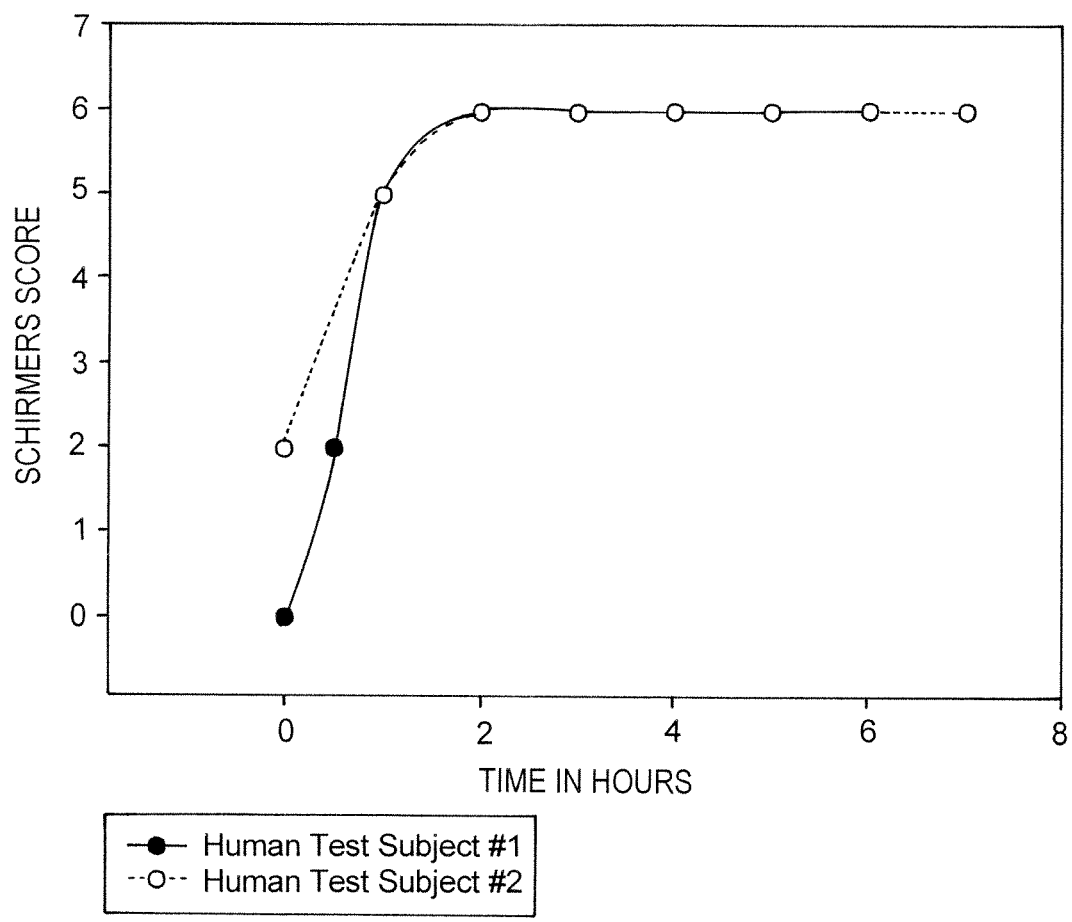
FIG. 2 is a graph showing the effect of transdermal application to an eyelid of a pilocarpine formulation containing caffeine on human tear production.

There was a rapid increase in tear production in both affected eyes in both subjects. There was an exponential increase in tear production in both patients within one hour of application that was sustained for six hours, as can be seen in FIG. 2.

Figure 3:
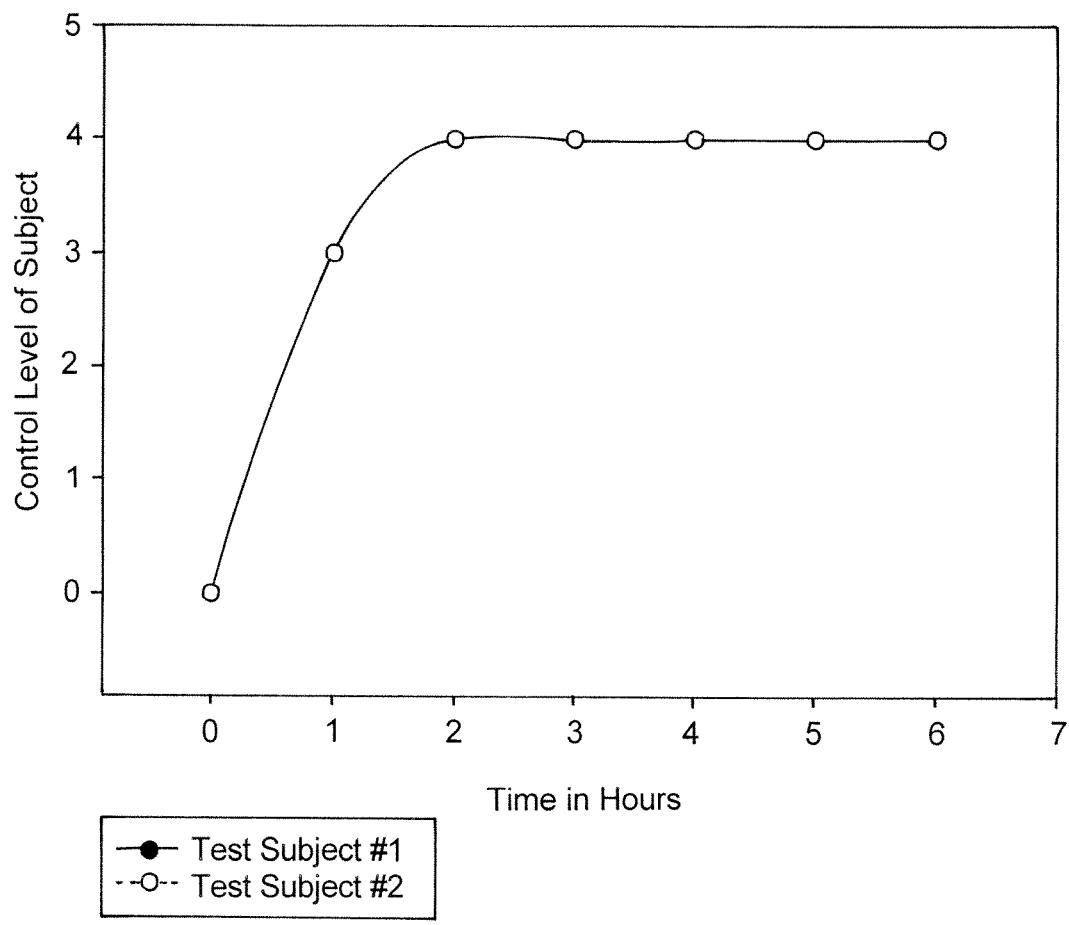
FIG. 3 is a graph showing the comfort level of subjects after transdermal upper eyelid application of a pilocarpine formulation with caffeine applied to one upper eyelid.

Prior to treatment both patients ranked their comfort level of the affected eye as 0 on a scale of 0 to 4 with 0 being the most irritated and 4 being the most comfortable. After application of pilocarpine, both patients reported a "cooling" feeling in the affected eye within thirty minutes of treatment, which was sustained for six to eight hours and a comfort level of 4 was achieved and maintained within two hours of treatment. A plot of the patients' comfort level is shown in FIG. 3.

Example 2

Intraocular Pressure

A normal human subject was selected to determine the effects of a single application of percutaneous upper eyelid application of a cream/lotion containing 0.2% timolol and 0.16% caffeine to the outer surface skin of one upper eyelid. The intraocular pressure was recorded in both the treated and untreated eye both before and after application of the composition. Additionally, the subject's vital signs, including pulse rate and blood pressure were recorded at the same time intervals as eye pressure was recorded. The effect of treatment was measured for over fifty two hours.

Figure 4:
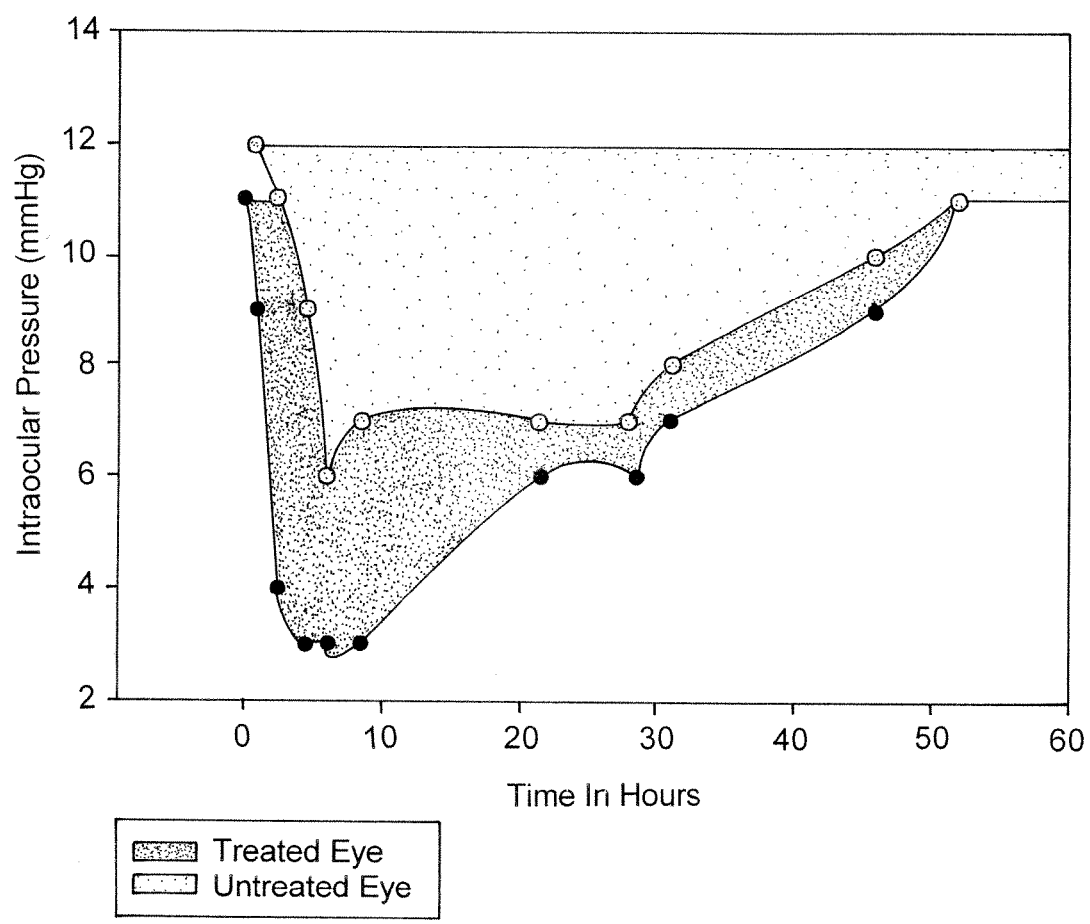
FIG. 4 is a graph showing the effect of transdermal upper eyelid application of a timolol plus caffeine formulation on intraocular pressure.

After a single application of timolol to one eyelid there was a rapid decline in intraocular pressure in both eyes as shown in FIG. 4. The treated eye showed a 73% drop in intraocular pressure within four hours of treatment, which returned to baseline eye pressure within 52 hours. The untreated eye rapidly dropped intraocular pressure by 50% within the same time frame as the treated eye, demonstrating the systemic absorption of timolol. The intraocular pressure of the untreated eye remained depressed for 52 hours, just as with the treated eye.

Figure 5:
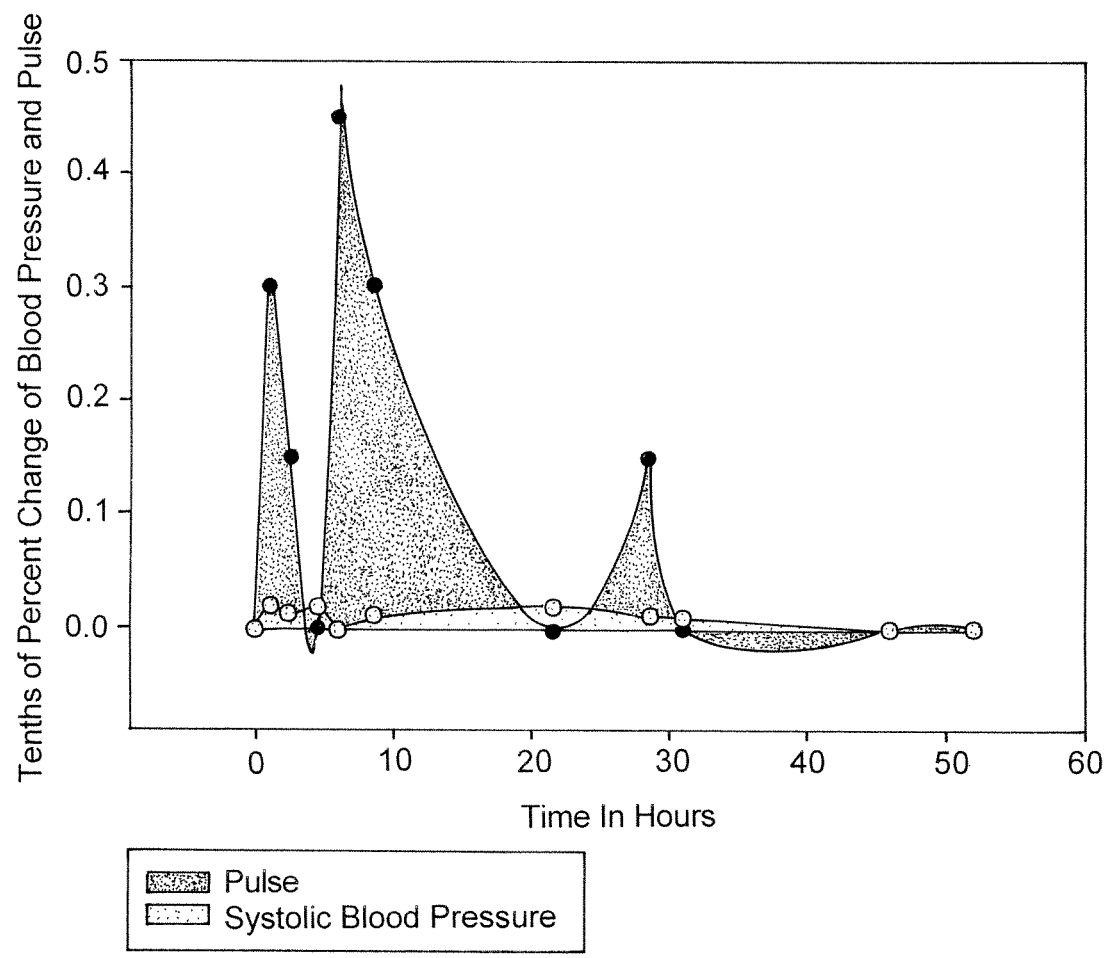
FIG. 5 is a graph showing the percentage change to human systolic blood pressure and pulse after application to one eyelid of a timolol plus caffeine.

Although the timolol was absorbed systemically to reach the untreated eye, the subject's vital signs showed stability within 0.04% for heart rate and 0.5% change for systolic pressure, as shown in FIG. 5.

Example 3

Effects of Topical Application of Physostigmine to One Eyelid

A normal human subject was selected to determine the effects of a single application of percutaneous upper eyelid application of a cream/lotion containing 5% physostigmine, a parasympathetic agonist, 0.16% caffeine to the outer surface skin of one upper eyelid. The effects on tear production, intraocular pressure and pupilary constriction were measured in both the treated and untreated eye both before and after application of the composition. Additionally, the subject's vital signs, including pulse rate and blood pressure were recorded at the same time intervals as eye pressure was recorded. The effect of treatment was measured for over twelve hours. Prior to treatment, the treated eye showed a dryness level of 0, while the untreated eye had a dryness level of 2 mm by Schirmers measurement.

Figure 6:
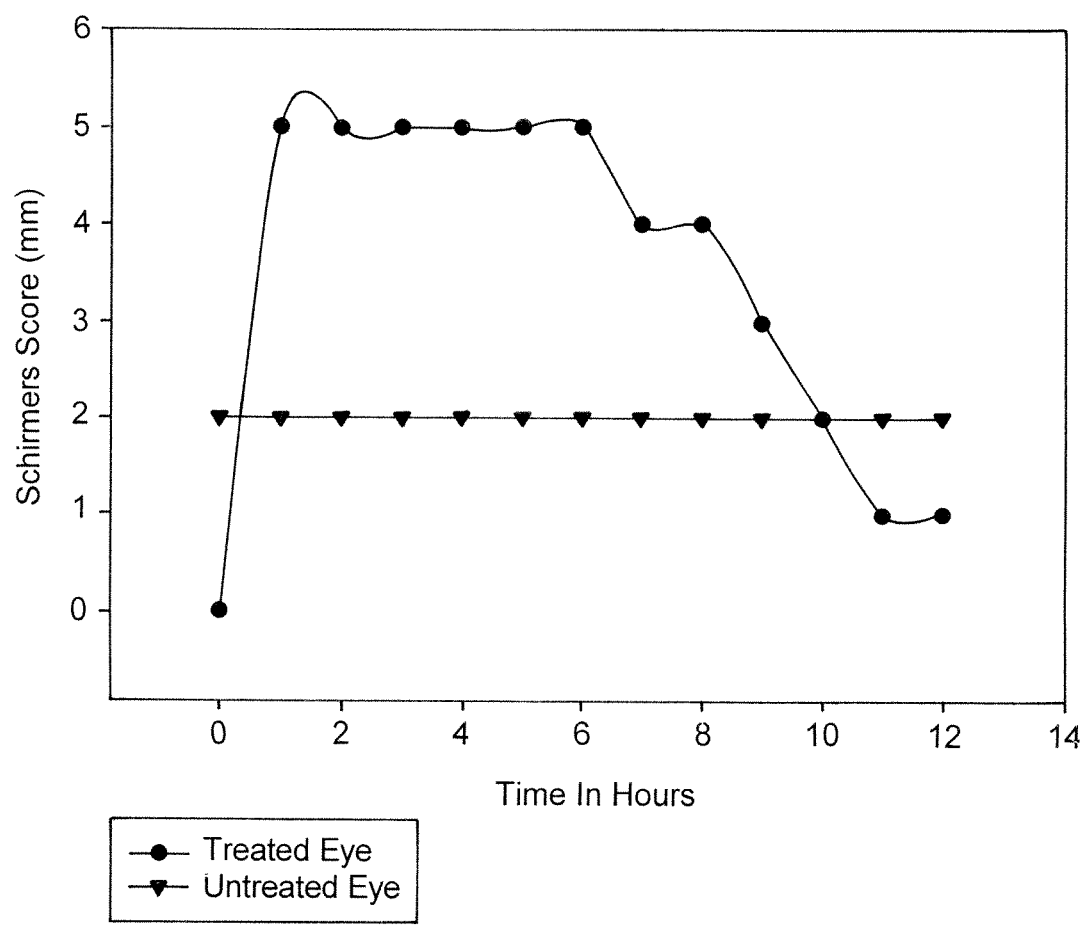
FIG. 6 is a graph showing the change in Schirmers score after upper eyelid application of a transdermaml physostigmine plus caffeine formulation.
Figure 7:
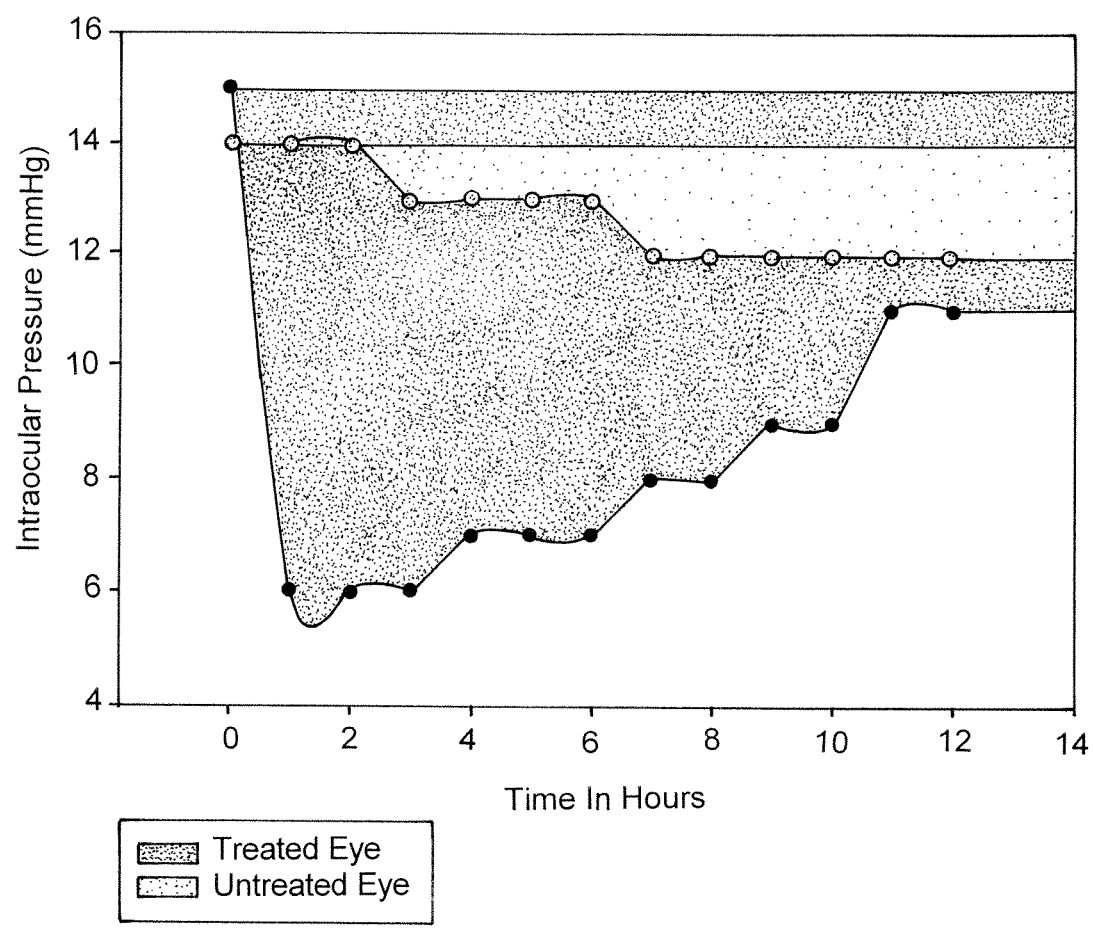
FIG. 7 is a graph showing the effects of upper eyelid application of a formulation containing physostigmine plus caffeine on intraocular pressure in the human eye.

After a single application of physostigmine to one eyelid there was a rapid increase in tear production from 0 to 5 mm in the treated eye by Schirmers measurement which declined over a period of 12 hours, as shown in FIG. 6. Tear production in the untreated eye remained unchanged over the same time period. The treated eye showed a 50% drop in intraocular pressure within an hour of treatment, which returned to baseline level within 12 hours. The intraocular pressure of the untreated eye remained unchanged over the testing period. These results are shown in FIG. 7.

Figure 8:
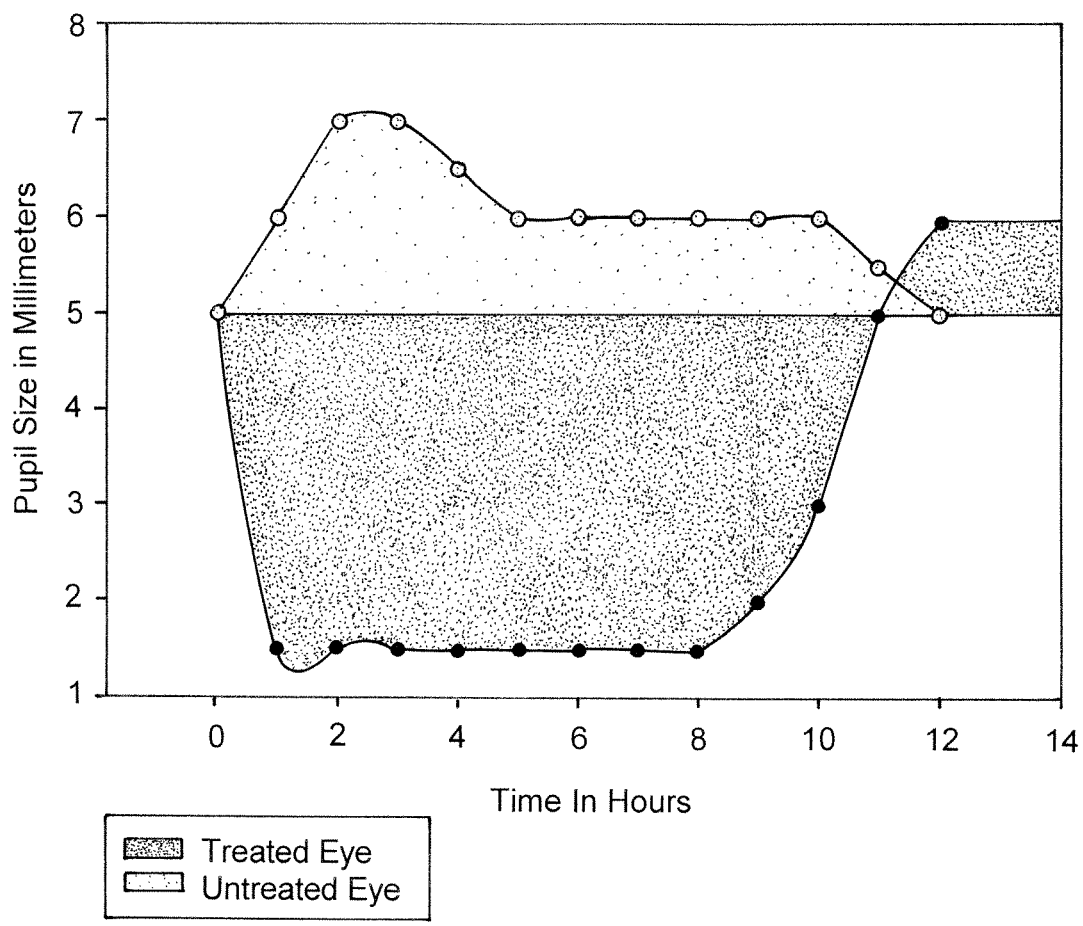
FIG. 8 is a graph showing change in pupil size after transdermal upper eyelid application of a physostigmine plus caffeine formulation.

The pupil of the treated eye rapidly became miotic (pinpoint pupil), while the pupil of the untreated eye increased in size, as shown in FIG. 8. The increase in pupil size in the untreated eye is the result of a systemic reaction—due to the systemic parasympathetic stimulation by a single physostigmine application, there was an increased sympathetic response to maintain the vital signs and normal cardiac output, resulting in pupilary dilation in the untreated eye.

Figure 9:
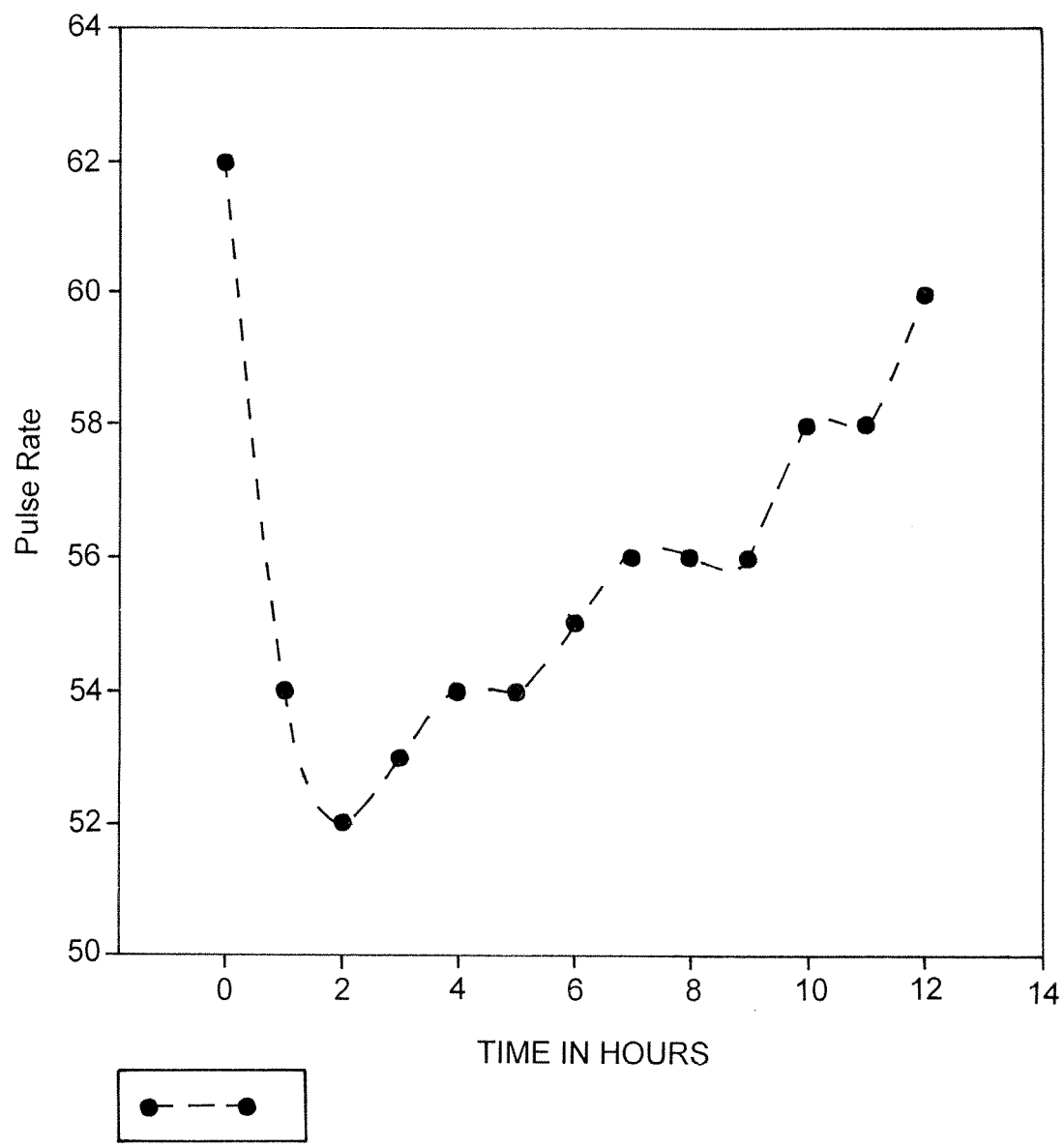
FIG. 9 is a graph showing the effect of upper eyelid transdermal monocular application of a physostigmine plus caffeine formulation on heart rate.
Figure 10:
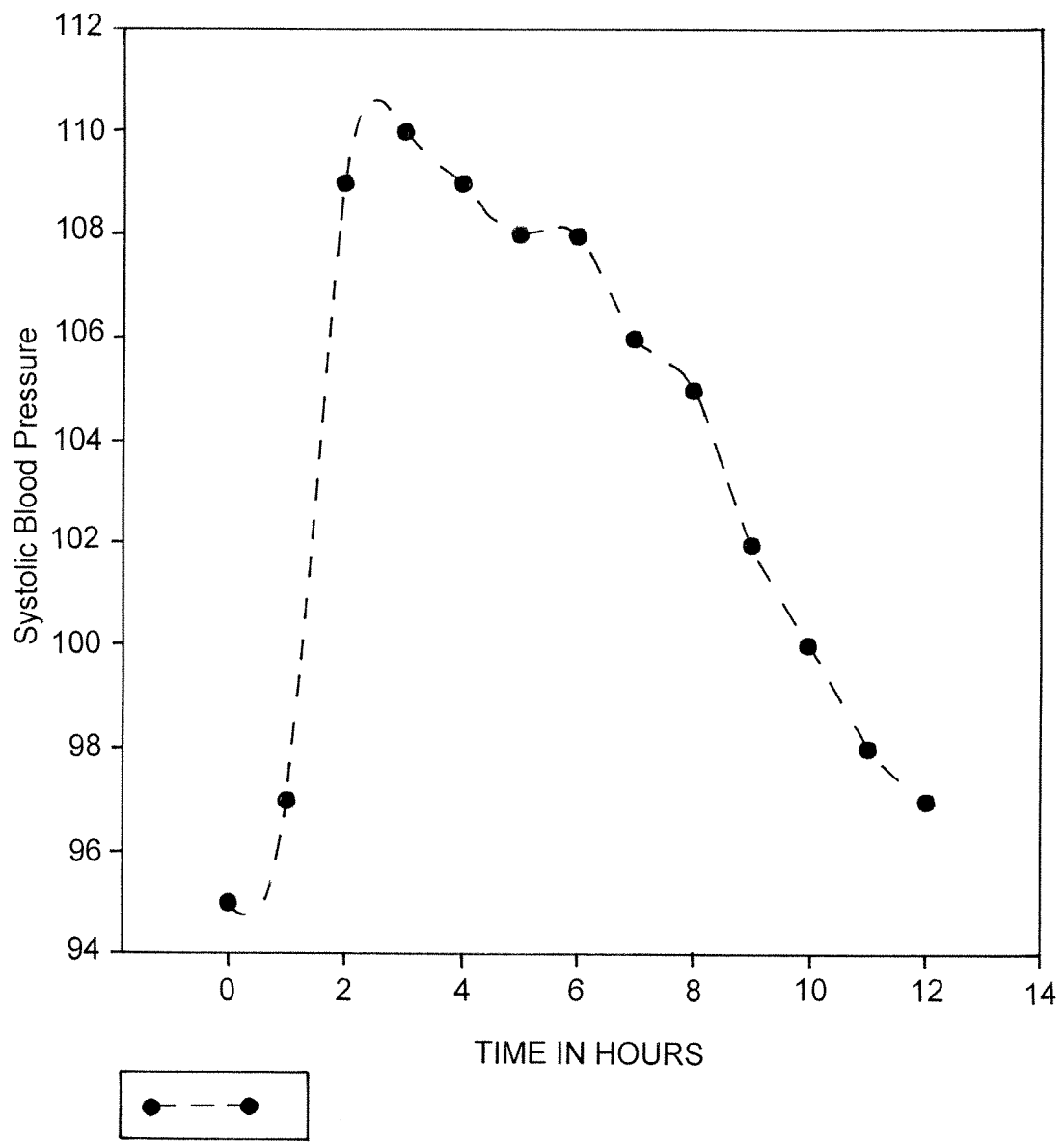
FIG. 10 is a graph showing the effect of transdemal application to an upper eyelid of a physostigmine plus caffeine formulation on human systolic blood pressure.

The systemic effects of application of physostigmine to one eyelid included an initial rapid decline in heart rate of 16% compared to baseline in the same time frame as the ocular effects. Physostigmine induced bradycaria in the subject, which was matched by a 15.7% increase in systolic blood pressure. The systemic effects are shown in FIGS. 9 and 10.

Example 4

Effect of Topical Application of Latanoprost to One Eyelid

A normal human subject was selected to determine the effects of a single percutaneous application to one upper eyelid of a cream/lotion containing 0.025% latanoprost, and 0.16% caffeine (applied to the outer surface skin of the upper eyelid). The effects on intraocular pressure were measured in both the treated and untreated eye both before and after application of the composition and were measured at intervals for three months. The results are shown in FIG. 11.

Figure 11:
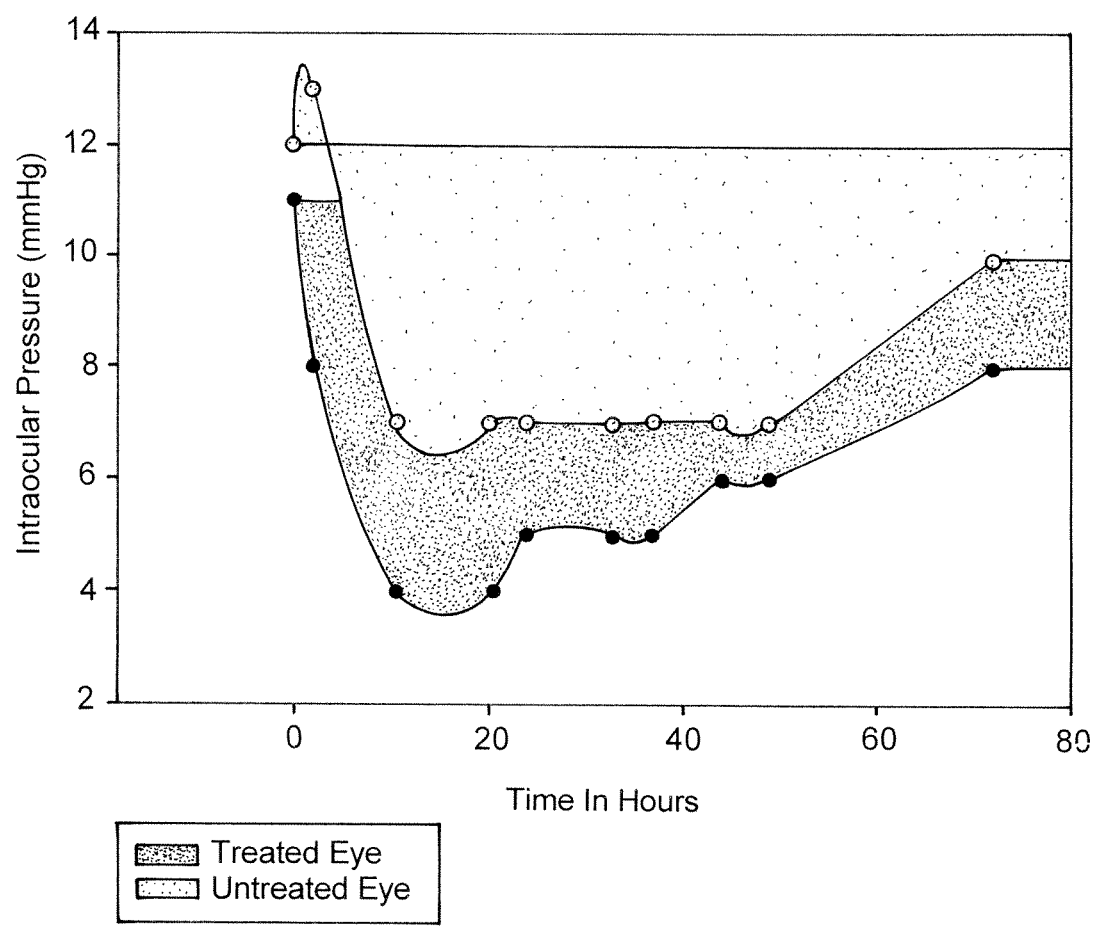
FIG. 11 is a graph showing the effect of upper eyelid transdermal monocular latanoprost application on human intraocular pressure.

FIG. 11 shows the decline in human intraocular pressure after a single application with transdermal latanoprost on the skin of one eyelid only. The treated eye showed a 53.8% drop in intraocular pressure in 10 hours and had not returned to pre-treatment levels over the three month observation period. The subject's intraocular pressure remained at 9 or below in the treated eye.

The untreated eye also dropped intraocular pressure by 36.3% within the same time frame and had not returned to baseline level after three months of observation. The subject's intraocular pressure remained at 10 or below in the untreated eye. The mechanism for this rapid decline in pressure in the untreated contralateral eye is by the pharmacological activity of latanoprost via systemic absorption.

Latanoprost is known to increase uveoscleral outflow by increasing scleral permability. These results demonstrate a significant sustained intraocular pressure reduction after a single transdermal application to one eyelid that is unknown in ophthalmology even with regular daily eye drop therapy and is probably due to a long lasting increase in scleral permability bilaterally. These results demonstrate that the present invention can be applied to treatment of the entire sclera of the eye as opposed to traditional treatment which treats only a small portion of the sclera which is accessible via the anterior segment of the eye.

The treated eye demonstrates a greater sustained drop in intraocular pressure than the untreated eye. The probable mechanism for this effect is the direct penetration of latanoprost to the posterior segment of the treated eye to change the outflow of the sclera in addition to the systemic blood flow carrying the drug to the treated eye and the untreated eye. The untreated eye demonstrates the effect achieved solely by systemic transport of latanoprost to the eyeball.

Example 5

Effect of Topical Application of Brimonidine to One Eyelid

Figure 12:
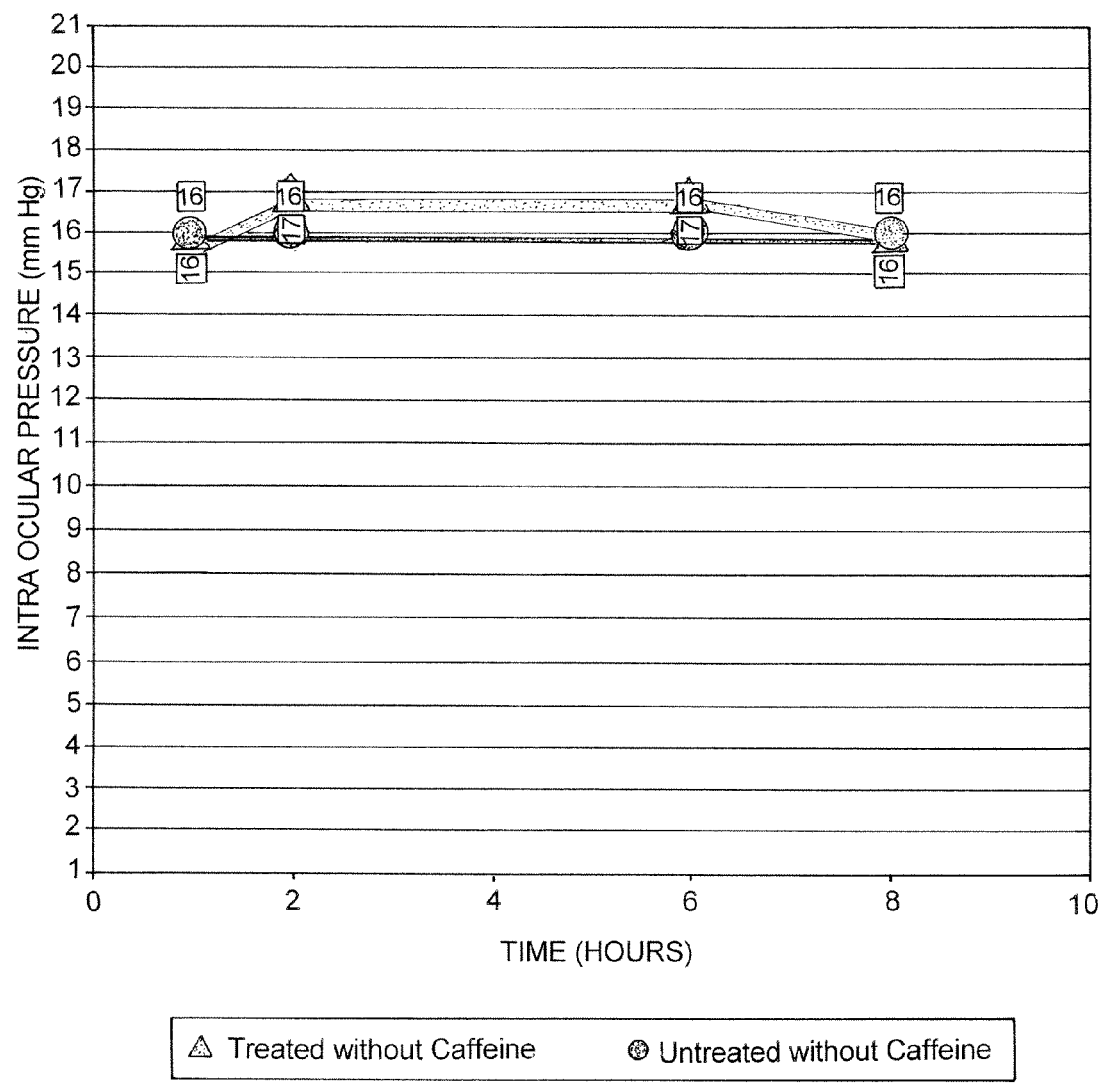
FIG. 12 is a graph showing the effect of topical application to an upper eyelid of a composition containing brimonidine (without caffeine) on human intraocular pressure.

A normal human subject was selected to demonstrate the effect of a single application of transdermal 0.05% Brimonidine lotion/cream without caffeine to the unaltered, untreated skin of the upper eyelid of one eye. The results are shown in FIG. 12. The intraocular pressure in both the treated and untreated eyes remains virtually unchanged over a period of seven hours and actually increased in the treated eye by one point.

Figure 13:
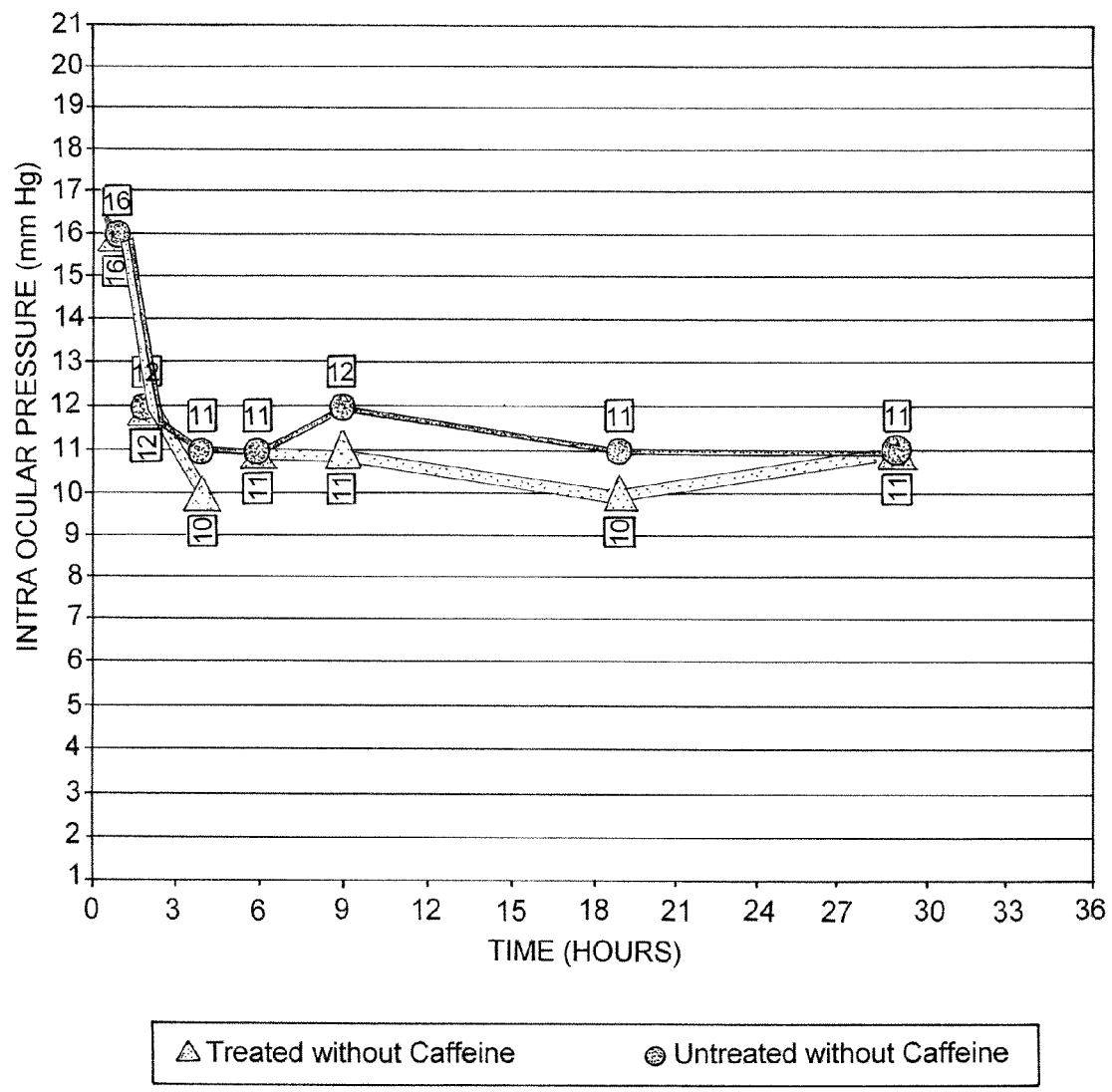
FIG. 13 is a graph showing the effect of topical application to an upper eyelid of a composition containing brimonidine plus caffeine on human intraocular pressure.

The same treatment was then repeated in the same subject using transdermal application to a single eyelid of a lotion/cream composition comprising 0.05% Brimonidine and 0.16% caffeine. The results are shown in FIG. 13. The intraocular pressure decreased symmetrically in both eyes by 25% within one hour after application and by 37.5% in the treated eye and 31.3% in the untreated eye in two hours. The effect of a single application to one eyelid was sustained in both eyes 28 hours later and was 31.3% less than baseline in both eyes. The effect lasted for two weeks and gradually wore off in 4 weeks. The graph shows the first 48 hours of this period.

Brimonidine is routinely administered as an eye drop which is typically dosed at least two times a day and produces about a 24% drop in intraocular pressure, with numerous well known side-effects per FDA data including itching, redness, and intolerance in up to 20% of patients necessitating stoppage of the drug. Additionally, according to FDA clinical data, 30% more patients had to discontinue the Brimonidine 0.2% eye drop use due to lack of clinical effect. In contrast, the results herein show a dramatic clinical effect without any side effects using only 25% of the concentration of the drug that the FDA tested.

Example 6

Topical Eyelid Application of Insulin/Humulin to a Non-Diabetic Subject

Figure 14:
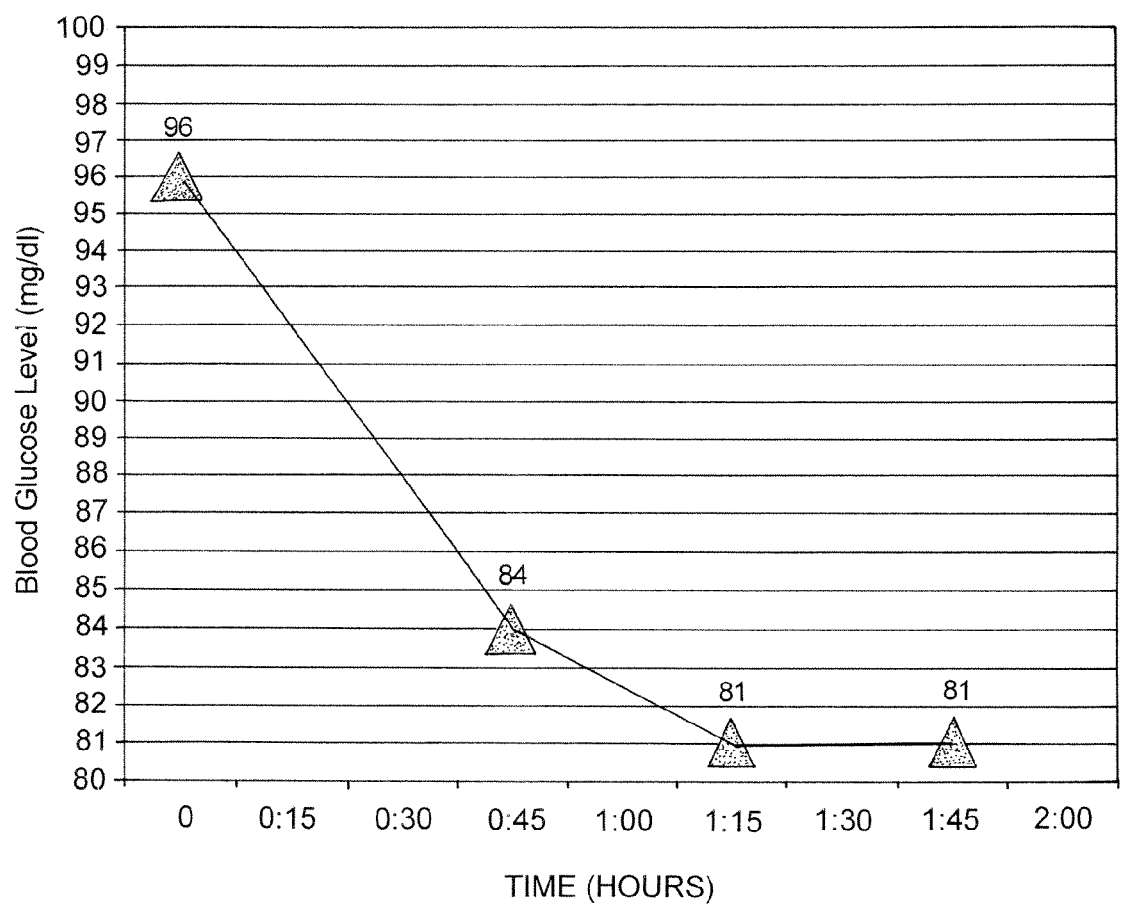
FIG. 14 is a graph showing the effect on a subject's blood glucose level of a single topical application of insulin/humulin to the upper eyelid of a normal subject.

A normal non-diabetic human subject was selected to demonstrate the effect of a single transdermal application of a lotion/cream containing 4 units of Insulin/Humulin and 0.16% caffeine to the unaltered, untreated normal skin of both upper eyelids. The results are shown in FIG. 14.

The subject's starting glucose level dropped by 12.5% in 45 minutes, and 15.6% in 1 hour and 15 minutes. The subject's blood sugar remained low at 81 and the subject reported hypoglycemic symptoms of sweating, tachycardia, dizziness, and headache. Consequently, the study was aborted and glucose was administered.

Example 7

Topical Eyelid Application of Insulin/Humulin to a Diabetic Subject

A non-insulin dependent diabetic human subject was selected to demonstrate the effect of a single transdermal application of a lotion/cream comprising 4 units Insulin/Humulin and 0.16% caffeine to the unaltered, untreated normal skin of a both upper eyelids of both eyes. All diabetic medications had been discontinued for 3 days prior to achieve systemic washout of oral medications. The results are shown in FIG. 15.

Figure 15:
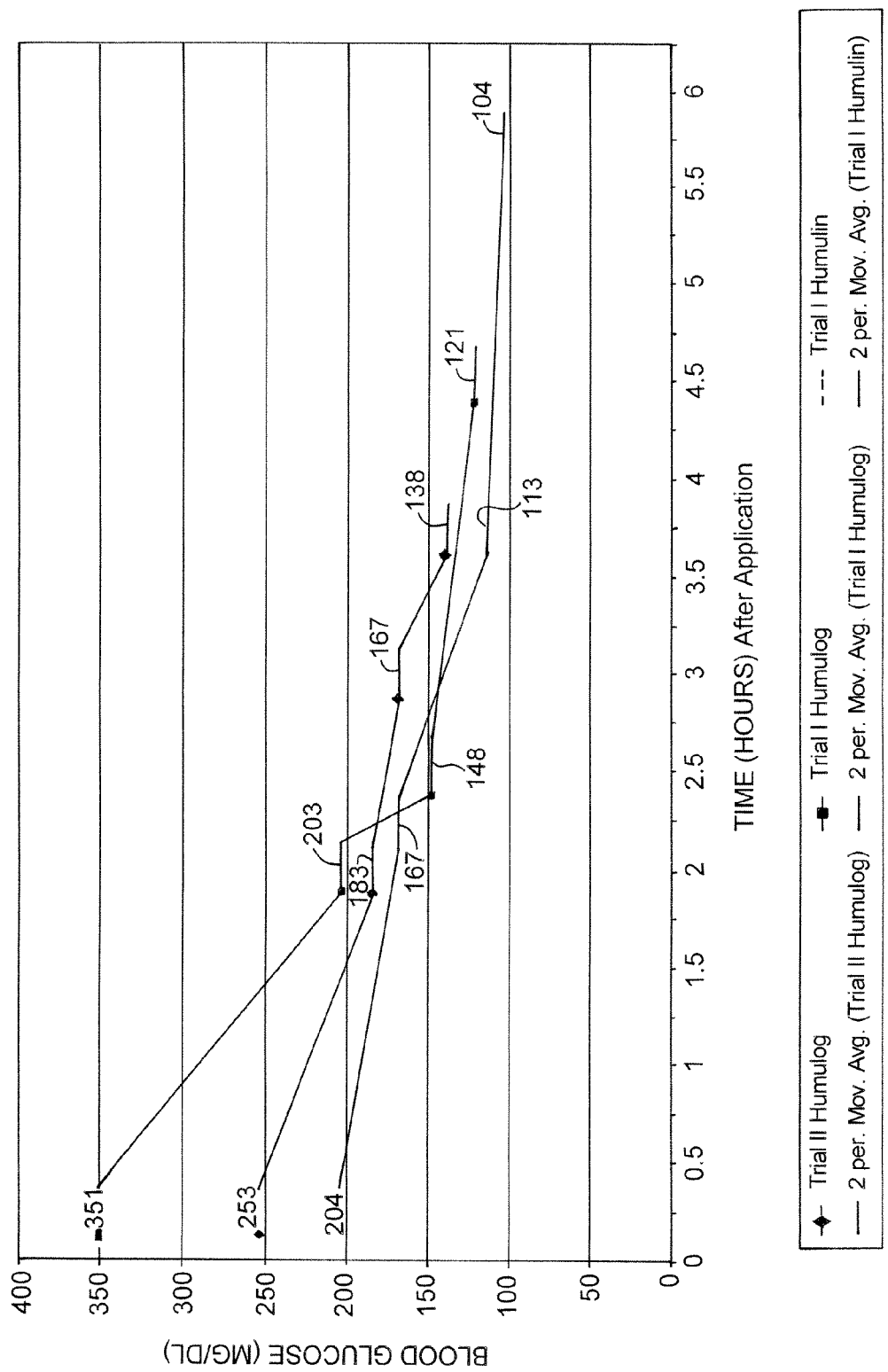
FIG. 15 is a graph showing the effects on the blood glucose levels of three diabetic human subjects of transdermal application to both upper eyelids of a composition containing insulin/humulin.

FIG. 15 shows the results of three trials: one trial was conducted with 4 units of Humulin and two trials were conducted with 4 units of Humulog. Humulog is insulin lispro which is a rapid and intermediate acting insulin of MW 5808 Daltons while Humulin is MW 5807.72 Daltons and is short acting.

In Trial I (Humulin) the subject's blood sugar dropped by 18.1% in 2 hours, 44.6% in 3.5 hours, and 49% in 5.5 hours to a normal range of blood glucose level.

In Trial II (Humulog), the subject's blood sugar response showed a more precipitous response with blood sugar decline of 45.4% in a 3.5 hour period despite a higher starting blood glucose level compared to Trial 1 of Humulin. Finally, Trial I of Humulog was also conducted to demonstrate the effect of Humulog at an even higher starting blood glucose level of 351 mg/dl. The subject's blood sugar dropped by 57.8% in 2.5 hours, and by 65.6% to a normal level of 121 in 4.5 hours.

These results demonstrate clinical effectiveness of the present invention at three different levels of diabetic range blood glucose levels in a human diabetic patient.

Example 8

Topical Eyelid Application of Lisinopril

An uncontrolled hypertensive human subject was selected to demonstrate the effect of a single transdermal application of a cream/lotion composition comprising 8 mg lisinopril and 0.16% caffeine to the unaltered, untreated normal skin of the upper eyelids of both eyes of the subject. All hypertensive medication (Telmisartan) had been discontinued for 10 days prior to achieve systemic washout. The patient's baseline blood pressures off all hypertensive medications were checked a total of 10 times on different days and times of the day. The blood pressure averaged a systolic of 145 and a diastolic of 85.

Figure 16:
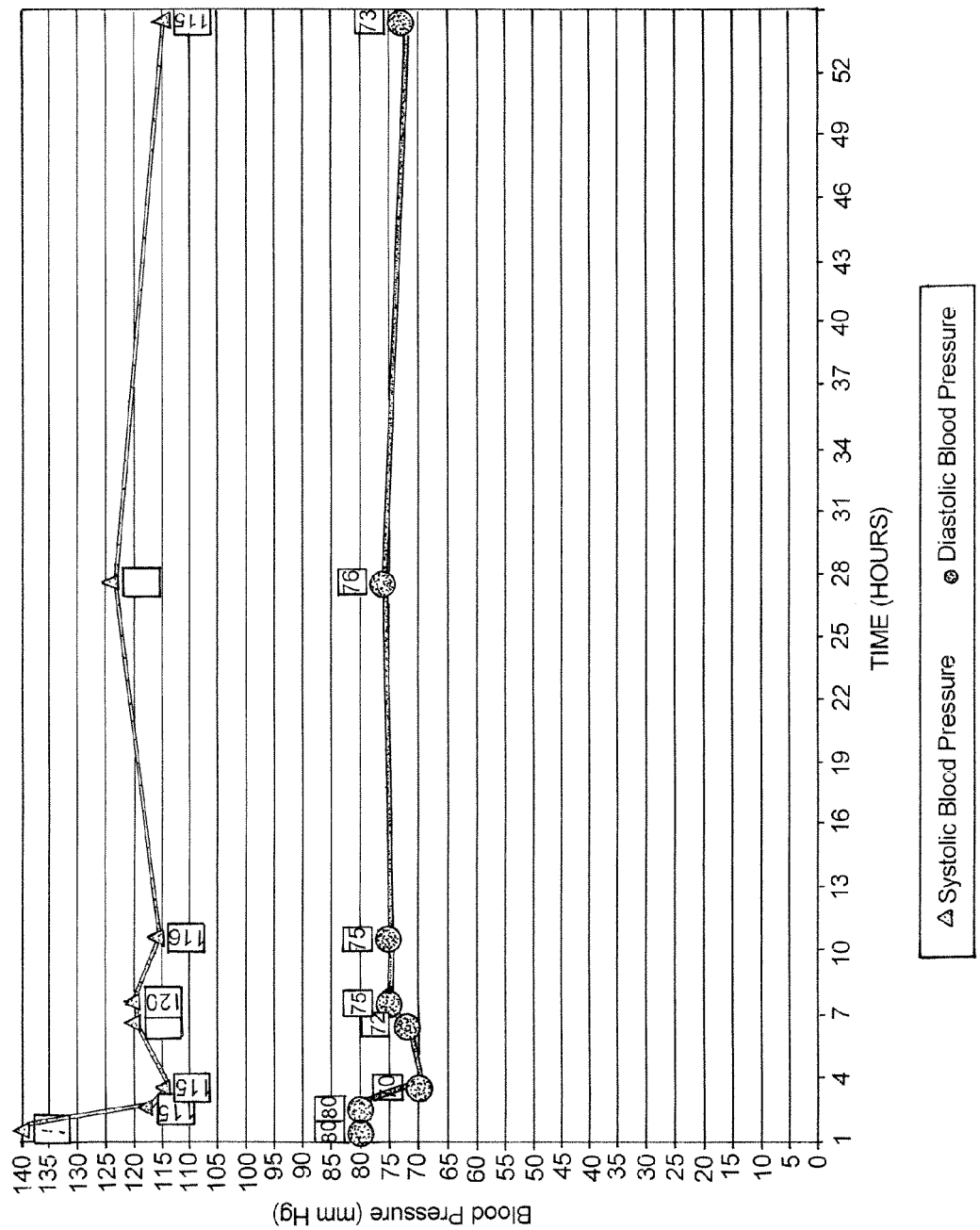
FIG. 16 is a graph showing the effect of application to one upper eyelid of a composition comprising lisinopril and caffeine on an untreated hypertensive humansubject's blood pressure.

The subject's blood pressure was re-measured immediately prior to applying the lisinopril/caffeine transdermal cream and was 140 systolic and 80 diastolic. The systolic blood pressure sustained a 15.7% drop in the first hour post application with the diastolic pressure remaining stable. Within two hours the systolic blood pressure declined further to 17.8% lower than baseline and the diastolic blood pressure for the first time, now declined by 12.5%. For the next 26 hours, the systolic blood pressure ranged from a drop of 11.4% to 17.1% less than baseline. The diastolic blood pressure also remained less than baseline and ranged from 5% to 12.5% less than baseline pre treatment diastolic blood pressure. Even 52 hours after application, the subject's blood pressure was 115 systolic and 73 diastolic, which represents a 17.8% drop in systolic blood pressure and an 8.75% drop in diastolic blood pressure compared to pretreatment blood pressure. These results are shown in FIG. 16.

The subject's heart rate during the trial showed a 16.6% increase during the first two hours of the trial during which time both the systolic and diastolic blood pressure declined by 17.8% and 12.5%, respectively. The percentage rise in heart rate nearly matches the percentage decline in systolic blood pressure, demonstrating the human body's ability to maintain perfusion by compensating for a pharmacologically induced decline in blood pressure (hypotension) by increasing heart rate via endogenous sympathetic compensatory mechanisms. This increase in heart rate is not sustained, since the patient's endogenous mechanisms to increase vascular resistance were probably activated leading to a subsequent increase in systolic blood pressure to 14.3% less than baseline and the heart rate went back to baseline. The diastolic blood pressure remained stable, but did not affect the heart rate as did the systolic blood pressure.

Example 9

Topical Eyelid Application of Pilocarpine

A human subject with preexisting symptomatic severe dry eye was selected for testing. The dry eye was quantified by Schirmer's tear testing and corneal findings. The subject received treatment with a single application of a cream/lotion comprising 1% pilocarpine without caffeine to the normal untreated, unaltered skin of one upper eyelid. The effect of treatment was then measured over six hours in tear production and comfort. The results are presented in FIGS. 17 and 18 and are described below.

Figure 17:
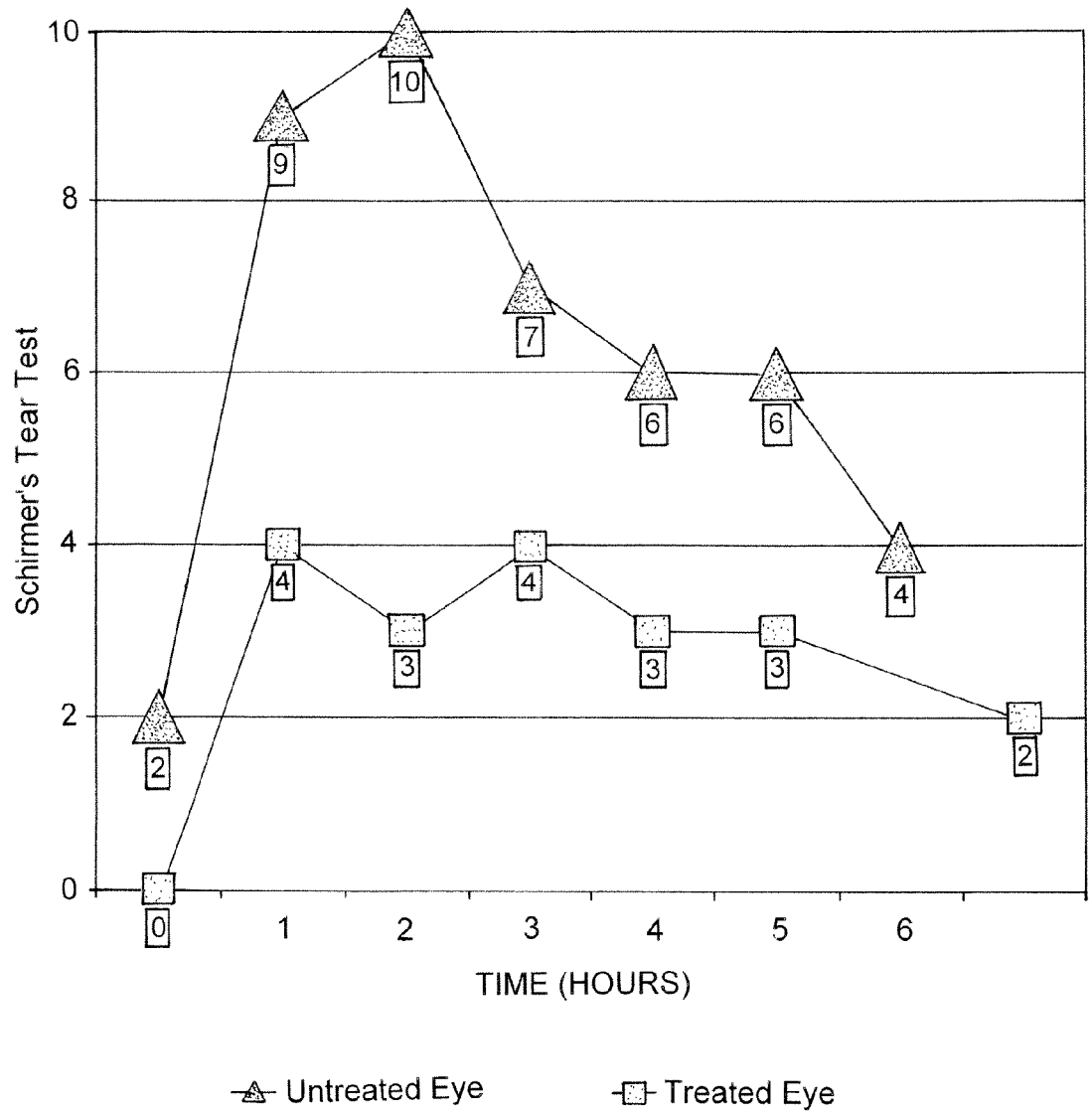
FIG. 17 is a graph showing the effect on tear production in the treated and untreated eye after topical application to one upper eyelid of a human of a composition comprising pilocarpine (without caffeine)

FIG. 17 demonstrates the rapid increase in human tear production in the setting of severe dry eye in a subject who was treated with a single transdermal application of pilocarpine lotion as described above. The treatment had been applied to the upper eyelid skin of the eye with a baseline tear production of zero. The subject showed an exponential increase in natural tear production within an hour; the increase was self sustained for six hours. Although the tear production was significant, it is somewhat less than that generated by the application of a combination of pilocarpine and caffeine (shown in FIG. 2).

There was also an increase in tear production in the untreated eye, which though severely dry also was not as bad as the baseline in the treated eye. The level of tear production in this eye approached normal after treatment.

Figure 18:
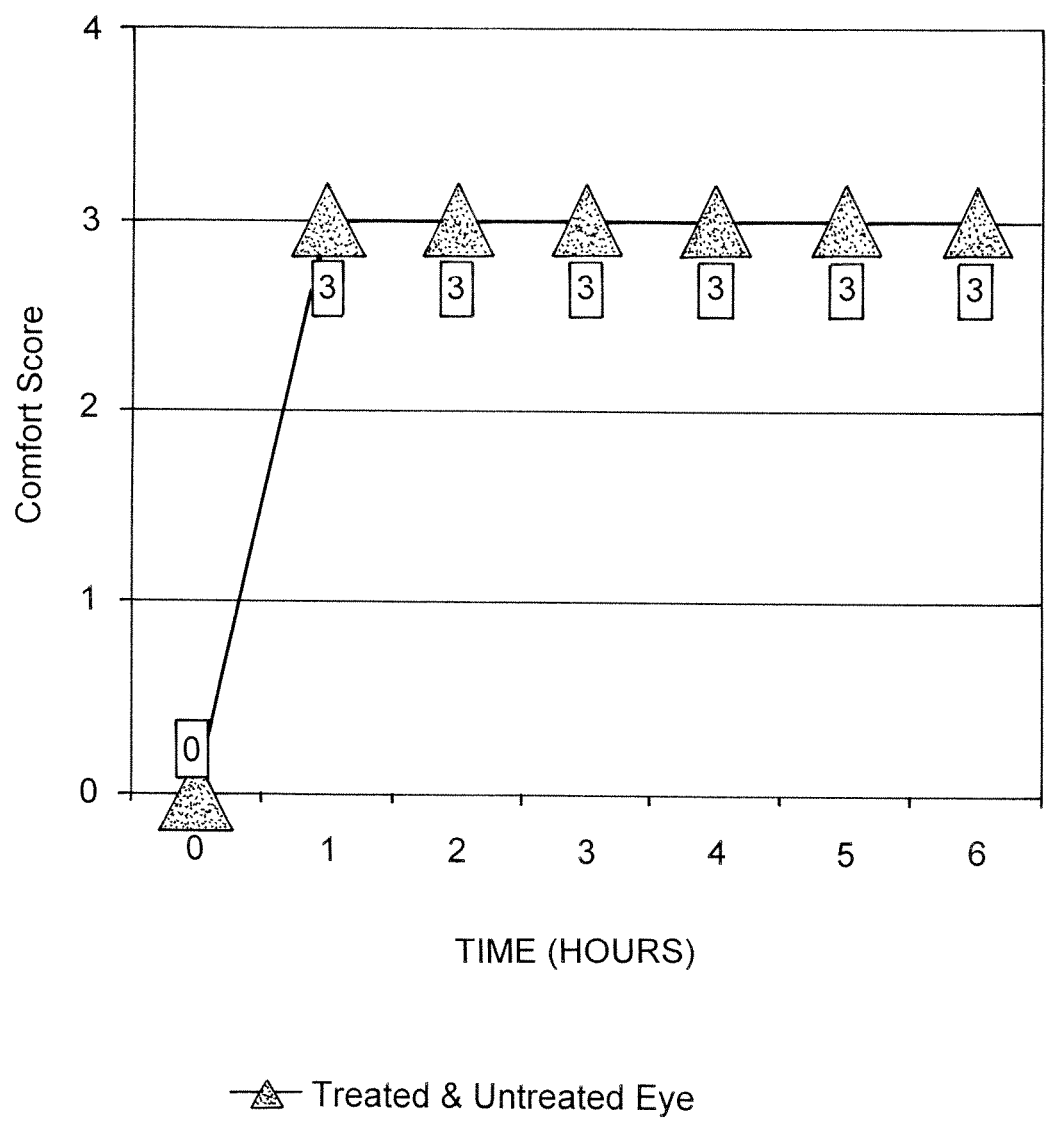
FIG. 18 is a graph showing the effect on comfort level in the treated and untreated eye of a human after application to one upper eyelid of a composition comprising pilocarpine (without caffeine).

FIG. 18 shows the subjective comfort level of the severe dry eye subject for the treated and untreated eye both before and after application of pilocarpine lotion/cream. Prior to treatment, the comfort level of the dry eye was ranked on a scale of 0 to 4; 0 being the most irritated and 4 being the most comfortable. After application of Pilocarpine lotion/cream, the subject reported an increase in comfort level to a constant score of three. However, the subject noted the absence of the "cooling" feeling with this treatment.

Example 9

Formulations

Each of the following formulations were made by the same basic formulation procedure:
1) In the main tank, added water, and BG Glycerin. Mixer was turned on and brought to medium speed.
2) Carbopol 940 was slowly sprinkled into the vortex. Continued mixing for 15-20 minutes until free of clumps.
3) Heated the mixture to 65 C and added phase C (preservatives)
4) In a separate mixing hot tank, the oil phase (Phase D) was combined and heated to 65° C.
5) When the main tank and premix tank reached 65° C., the oil phase was added to the main tank.
6) PEG 8 and optionally caffeine were added with continued mixing it until coos down to 50° C.
7) In separate bucket, a 25% sodium hydroxidesolution was prepared with deionized water, mixing until sodium hydroxide dissolved.
(Cautious: Be sure to wear sleeve, lab coat and safety goggles when preparing this solution)
8) The sodium hydroide solution was poured into the main batch. Mixing speed was turned to high speed until a slight vortex was achieved.
9) The batch was cooled to 40-50° C. and then Tetrasodium EDTA was added and mixed for 5-10 minutes.
10) Add Saccharide Isomerate and mix until the batch is homogenous.
11) A top and bottom sample were obtained for analysis.
12) Mixed in the listed drug or therapeutic agent, partially dehydrated into 0.005 gm of the formulation.

The following are representative examples of gel, cream, ointment and vesicle based topical bases used in the examples set forth above.

A. Gel

| Excipient | Use |
| --- | --- |
| Hydroxyethylcellulose | Viscosity modifier |
| Ethanol | Permeation enhancer |
| Methyl paraben | Preservative |
| Propyl paraben | Preservative |
| Water/Buffer | |

B. Cream

| Excipient | Use |
| --- | --- |
| Stearic acid | Oily phase |
| Propylene glycol monostearate | Emulsifier |
| Propylene glycol | Humectant |
| Isopropyl palmitate/Isopropyl myristate | Permeation enhancer |
| Polysorbate 60 | Emulsifier |
| Methyl paraben | Preservative |
| Propyl paraben | Preservative |
| Water/Buffer | |

C. Ointment

| Excipient | Use |
| --- | --- |
| White petrolatum | Oily phase |
| White wax | Oily phase |
| Stearyl alcohol | Emulsifier |
| Cholesterol | Emulsifier |
| Isopropyl palmitate/Isopropyl myristate | Permeation enhancer |

D. Ethosomes (Vesicular Technology)

| Excipient | Use |
| --- | --- |
| Distearyl phosohotidyl choline | Vesicle forming agent |
| Ethanol | Skin permeation enhancer |
| Cholesterol | Vesicle membrane stabilizer |
| Carbopol | Gel forming agent |
| Water | |

Formulations Used in the Examples:

Pilocarpine 1% Formulation Without Caffeine

| Phase | Ingredients | % by WT |
| --- | --- | --- |
| A | Water (Deionized) | 65.7000 |
| D | Caprylic/capric Triglyceride | 15.6500 |
| D | C12-20 Acid PEG-8 Ester | 5.0000 |
| A | Butylene Glycol | 4.4400 |
| A | Glycerin | 3.2500 |
| H | Saccharide Isomerate | 2.0000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |

Pilocarpine 1% Formulation with 0.16% Caffeine

| Phase | Ingredients | % by WT |
|---|---|---|
| A | Water (Deionized) | 65.7000 |
| D | Caprylic/capric Triglyceride | 15.6500 |
| D | C12-20 Acid PEG-8 Ester | 5.0000 |
| A | Butylene Glycol | 4.4400 |
| A | Glycerin | 3.2500 |
| H | Saccharide Isomerate | 2.0000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |
| E | Caffeine | 0.16 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Physostigmine (5%) Formulation with Caffeine

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |
| E | Caffeine | 0.16 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Timolol (0.25%) Formulation with Caffeine

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |
| E | Caffeine | 0.16 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Lisinopril Formulation

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |
| E | Caffeine | 0.16 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Latanoprost Formulation without Caffeine

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |

| Phase | Ingredients | % by WT |
|---|---|---|
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Latanoprost Formulation with Caffeine

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |
| E | Caffeine | 0.16 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Brmonidine (Alphagan P) Formulation With Caffeine

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |
| E | Caffeine | 0.16 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

Brimonidine (Alphagan P) Formulation without Caffeine

| Phase | Ingredients | % by WT |
|---|---|---|
| A | Water (Deionized) | 657000 |
| D | Caprylic/capric Triglyceride | 156500 |
| D | C12-20 Acid PEG-8 Ester | 50000 |
| A | Butylene Glycol | 44400 |
| A | Glycerin | 32500 |
| H | Saccharide Isomerate | 20000 |
| E | PEG-8 | 1.75 |
| D | Cetyl Alcohol | 1 |
| B | Carbomer 940 | 0.3 |
| G | Tetrasodium EDTA | 0.2 |
| F | Sodium Hydroxide (25% Solution) | 0.3 |
| C | Methylparaben | 0.2 |
| C | Propylparben | 0.05 |

| TEST | PROPOSED SPECIFICATION |
|---|---|
| Appearance | White Viscous Solution |
| Color | White Viscous Solution |
| Order | Fragrance Free |
| Clarity | Opaque |
| pH | 5.7-6.7 |
| % solids | 25.7-28.5 |
| Viscosity | 57,000-96,000 cps |

What is claimed is:

1. A method for treating an ophthalmic condition of the surface or interior of the eyeball or an ocular gland in a human patient in need thereof comprising topically administering a composition to the outer surface of at least one upper eyelid of the patient, said composition comprising (1) a therapeutically effective amount of at least one therapeutic agent effective for treatment of the ophthalmic condition, (2) from 0.001% to 50 wt % of a muscle fasciculating agent selected from the group consisting of caffeine, theobromine, theophylline and pentoxifyline and (3) a pharmaceutically acceptable carrier, wherein said therapeutic agent is selected from the group consisting of anti-glaucoma agents, vasoconstrictors, vasodilators, anticholinergic agents, cholinergic agents, α-agonists, β-agonists, anti-inflammatories, secretogues, antibiotics, mast cell stabilizers and combinations thereof, wherein said administration results in delivery of the therapeutic agent across the eyelid and to target tissue of the eyeball or ocular gland.

2. The method of claim 1 wherein the composition is applied to one upper eyelid of the patient.

3. The method of claim 1 wherein the therapeutic agent is a vasoconstrictor.

4. The method of claim 3 wherein the vasoconstrictor is applied to the perimeter of the outer surface of at least one eyelid of the patient.

5. The method of claim 1 wherein a vasodilator is the sole active therapeutic agent applied to the at least one eyelid of the patient.

6. The method of claim 1 wherein the composition further comprises a penetrating agent.

7. The method of claim 1 wherein the muscle fasciculating agent is caffeine.

8. The method of claim 7 wherein the composition comprises from 10 mg to 500 mg caffeine.

9. The method of claim 1 wherein the ophthalmic condition is glaucoma and wherein the at least one therapeutic agent is a secretogue selected from the group consisting of timolol, brimonidine and latanoprost, and the muscle fasciculating agent is caffeine.

10. The method of claim 1 wherein the ophthalmic condition is dry eye and wherein the at least one therapeutic agent is pilocarpine and the muscle fasciculating agent is caffeine.

11. The method of claim 1 wherein the composition further comprises an ionotropic agent.

12. The method of claim 1 wherein the therapeutic agent comprises a combination of a vasodilator and a vasoconstrictor.

13. The method of claim 1 wherein the composition is applied to the outer surface of at least one eyelid in the form of a gel, lotion, cream, spray, foam, adhesive formulation, plaster, film, strip, poultice or ointment.

14. The method of claim 1 wherein application of the composition to the outer surface of at least one eyelid results in delivery of the therapeutic agent to the posterior segment of the eyeball.

15. The method of claim 1 wherein application of the composition to the outer surface of one eyelid results in delivery of the therapeutic agent to the contralateral eye.

16. The method of claim 1 wherein the ophthalmic condition is seasonal allergy or allergic eye disease.

17. The method of claim 1 wherein said administration results in sustained release of the at least one therapeutic agent into the eyeball or ocular gland or on the surface of the eyeball.

18. The method of claim 1 wherein the composition further comprises a permeating agent.

19. A method of treating an ophthalmic condition of the surface or interior of the eyeball or an ocular gland in a human patient in need thereof comprising applying to the outer surface of at least one eyelid of the patient a first composition comprising (1) a therapeutically effective amount of a first therapeutic agent for treatment of the ophthalmic condition, (2) from 0.001% to 50 wt % of a muscle fasciculating agent selected from the group consisting of caffeine, theobromine, theophylline and pentoxifyline, and (3) a pharmaceutically acceptable carrier; and applying to the outer surface of at least one eyelid a second composition comprising (1) a therapeutically effective amount of a second therapeutic agent for treating the ophthalmic condition, 2) from 0.001% to 50 wt % of a muscle fasciculating agent selected from the group consisting of caffeine, theobromine, theophylline and pentoxifyline, and (3) a pharmaceutically acceptable carrier; wherein said second therapeutic agent is different from said first therapeutic agent, and wherein administration of said first and second compositions results in delivery of each of the first and second therapeutic agent across the at least one eyelid and to target tissue of the eyeball or ocular gland.

20. The method of claim 19 wherein both the first and second compositions comprise a muscle fasciculating agent.

21. The method of claim 20 wherein the first and second compositions are each applied to the outer surface of a different eyelid of the patient.

22. The method of claim 19 wherein the first composition comprises a vasodilator and the second composition comprises a vasoconstrictor.

23. The method of claim 22 wherein the vasodilator and the vasoconstrictor are applied to different regions of the outer surface of the at least one eyelid.

24. The method of claim 22 wherein the vasoconstrictor is applied to the perimeter of the outer surface of the at least one eyelid.

25. The method of claim 19 wherein the first composition, second composition or both further comprises an ionotropic agent.

* * * * *